United States Patent
Tsuboi et al.

(10) Patent No.: US 9,259,159 B2
(45) Date of Patent: Feb. 16, 2016

(54) INFORMATION PROCESSING APPARATUS, INFORMATION PROCESSING METHOD, AND COMPUTER PROGRAM FOR MEASURING EARDRUM TEMPERATURE

(71) Applicant: Sony Corporation, Tokyo (JP)

(72) Inventors: Toshimitsu Tsuboi, Tokyo (JP); Akichika Tanaka, Chiba (JP); Takeshi Asakawa, Chiba (JP); Naoya Sazuka, Tokyo (JP); Seiji Wada, Kanagawa (JP)

(73) Assignee: SONY CORPORATION, Tokyo (JP)

(*) Notice: Subject to any disclaimer, the term of this patent is extended or adjusted under 35 U.S.C. 154(b) by 212 days.

(21) Appl. No.: 13/847,113

(22) Filed: Mar. 19, 2013

(65) Prior Publication Data

US 2013/0296685 A1   Nov. 7, 2013

(30) Foreign Application Priority Data

Mar. 29, 2012   (JP) ................. 2012-076046

(51) Int. Cl.
*A61B 5/01* (2006.01)
*A61B 5/00* (2006.01)
*G01J 5/08* (2006.01)
*G01J 5/04* (2006.01)
*G01J 5/00* (2006.01)

(52) U.S. Cl.
CPC ............. *A61B 5/01* (2013.01); *A61B 5/0059* (2013.01); *A61B 5/6817* (2013.01); *G01J 5/0011* (2013.01); *G01J 5/049* (2013.01); *G01J 5/089* (2013.01); *G01J 5/0896* (2013.01)

(58) Field of Classification Search
CPC ...... A61B 5/0059; A61B 5/01; A61B 5/6817; G01J 5/0011; G01J 5/049; G01J 5/089; G01J 5/0896
See application file for complete search history.

(56) References Cited

U.S. PATENT DOCUMENTS

| | | | |
|---|---|---|---|
| 6,832,989 B2 | 12/2004 | Sato et al. | |
| 7,108,419 B2* | 9/2006 | Harr | 374/121 |
| 7,369,686 B2 | 5/2008 | Yokono et al. | |
| 7,574,037 B2 | 8/2009 | Hidai et al. | |
| RE43,873 E | 12/2012 | Hidai et al. | |
| 2003/0067957 A1* | 4/2003 | Ko et al. | 374/130 |
| 2004/0225207 A1* | 11/2004 | Bae et al. | 600/340 |
| 2009/0124873 A1* | 5/2009 | Uchida | 600/310 |

FOREIGN PATENT DOCUMENTS

| | | |
|---|---|---|
| JP | 2671946 B2 | 11/1997 |
| JP | 11-028194 A | 2/1999 |
| JP | 2002-340681 A | 11/2002 |
| JP | 2005-157679 A | 6/2005 |
| JP | 3896807 B2 | 3/2007 |
| JP | 4333364 B2 | 9/2009 |
| JP | 4517633 B2 | 8/2010 |

* cited by examiner

*Primary Examiner* — Ruth S Smith
(74) *Attorney, Agent, or Firm* — Hazuki International, LLC

(57) ABSTRACT

There is provided an information processing apparatus including an eardrum recognition unit configured to recognize a position of an eardrum based on image information regarding the eardrum, a temperature measurement unit configured to acquire a temperature within an external ear canal including the eardrum, and a temperature processing unit configured to determine a temperature of the eardrum based on a recognition result of the eardrum recognition unit and a measured temperature of the temperature measurement unit.

11 Claims, 21 Drawing Sheets

INFORMATION PROCESSING APPARATUS, INFORMATION PROCESSING METHOD, AND COMPUTER PROGRAM FOR MEASURING EARDRUM TEMPERATURE

CROSS-REFERENCE TO RELATED APPLICATION

The present application claims priority from Japanese Patent Application No. JP 2012-076046 filed in the Japanese Patent Office on Mar. 29, 2012, the entire content of which is incorporated herein by reference.

BACKGROUND

The present disclosure relates to an information processing apparatus, an information processing method, and a computer program that measure an eardrum temperature.

Recently, a type of clinical thermometer that measures a body temperature by measuring radiant heat emitted from an eardrum has been proposed. In such a clinical thermometer, a sensor that measures the radiant heat of the eardrum from an external ear canal is inserted and the radiant heat emitted from the eardrum is measured in a non-contact form. For example, in Japanese Patent No. 2671946, an eardrum temperature measurement apparatus for inserting a sensor unit including a first temperature sensor, which detects infrared rays from an eardrum and generates an output voltage in proportion to a temperature difference between an ambient temperature and an eardrum temperature, and a second temperature sensor, which detects a temperature around the first temperature sensor, into an external ear canal is disclosed. A package in which the sensor unit is housed can be held by a support including silicone rubber having a shape that approximately fills between an external ear canal entrance and a first bent portion of the external ear canal. The package can be positioned inside the external ear canal by inserting the support into the external ear canal.

For stable fixing inside the external ear canal, a shape of an insertion portion of a thermometer that measures radiant heat of the eardrum in the related art, a shape along the external ear canal (for example, Japanese Patent No. 2671946 and Japanese Unexamined Patent Application Publication No. 2002-340681) or a cone shape (for example, Japanese Unexamined Patent Application Publication No. H11-28194) is generally formed. In addition, for measurement of a distance from the eardrum to the temperature sensor, a method using distance measurement by laser irradiation or bouncing of sound waves is general.

SUMMARY

However, in Japanese Patent No. 2671946 and Japanese Unexamined Patent Application Publication Nos. 2002-340681 and H11-28194 described above, only one measurement operation for a short time is assumed, and continuous measurement for a long time is not considered. Because the thermometer falls out of the ear if the insertion portion of the thermometer is not firmly pressed into the eardrum at the external ear canal entrance side, it is difficult to constantly hold a direction of the sensor unit inserted into the external ear canal or the user may also experience a large sense of discomfort.

In addition, in Japanese Patent No. 3896807, an infrared clinical thermometer that determines whether an insertion state of a probe into the external ear canal is appropriate by detecting infrared rays radiated from the eardrum using a detection sensor is disclosed. In the infrared clinical thermometer of Japanese Patent No. 3896807, a body temperature is measured only when the probe is accurately inserted into the external ear canal. However, in the infrared clinical thermometer of Japanese Patent No. 3896807, a predetermined temperature range is set as a measurable range and hence it is difficult to say that radiant heat of the eardrum is accurately measured.

It is desirable to provide a technique of more accurately measuring an eardrum temperature so as to measure a deep body temperature of a human body.

According to an embodiment of the present disclosure, there is provided an information processing apparatus including an eardrum recognition unit configured to recognize a position of an eardrum based on image information regarding the eardrum, a temperature measurement unit configured to acquire a temperature within an external ear canal including the eardrum, and a temperature processing unit configured to determine a temperature of the eardrum based on a recognition result of the eardrum recognition unit and a measured temperature of the temperature measurement unit.

According to an embodiment of the present disclosure, there is provided an information processing method including recognizing a position of an eardrum based on image information regarding the eardrum, acquiring a temperature within an external ear canal including the eardrum, and determining a temperature of the eardrum based on a recognition result of the position of the eardrum and the acquired temperature.

According to an embodiment of the present disclosure, there is provided a computer program for causing a computer to function as an information processing apparatus including an eardrum recognition unit configured to recognize a position of an eardrum based on image information regarding the eardrum, a temperature measurement unit configured to acquire a temperature within an external ear canal including the eardrum, and a temperature processing unit configured to determine a temperature of the eardrum based on a recognition result of the eardrum recognition unit and a measured temperature of the temperature measurement unit.

In accordance with the embodiments of the present disclosure described above, an eardrum temperature can be reliably measured by recognizing an eardrum from an image and performing temperature measurement.

DETAILED DESCRIPTION OF THE EMBODIMENT(S)

Figure 1:
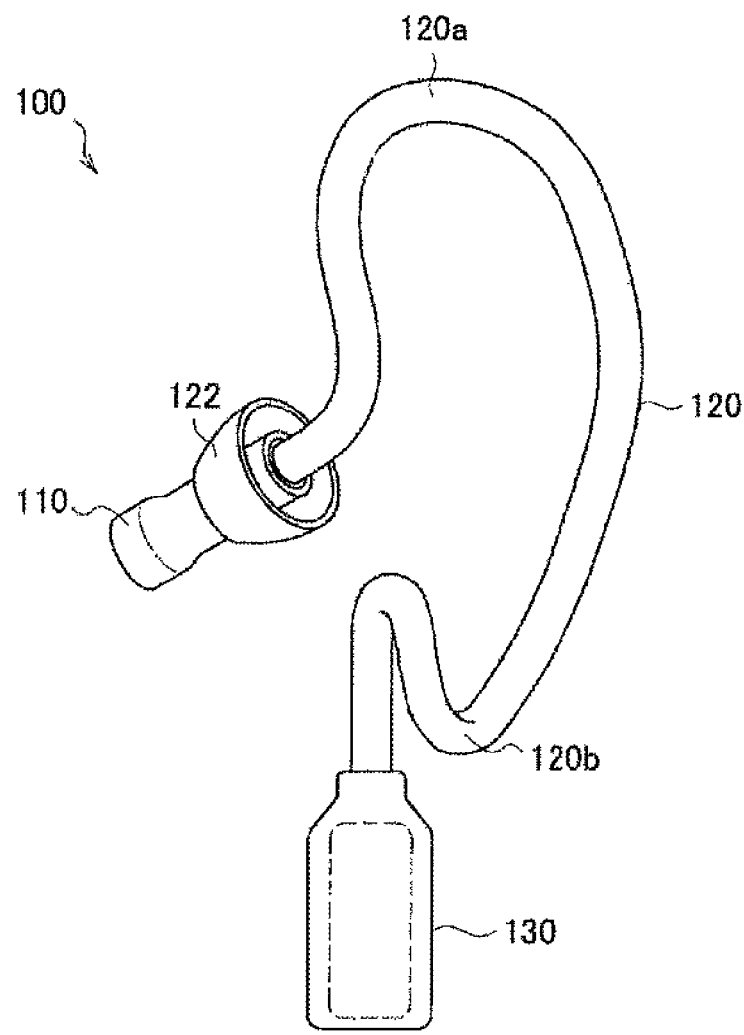
FIG. 1 is an external appearance diagram illustrating a configuration of an auricle-worn device in accordance with an embodiment of the present disclosure.

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted.

Description will be given in the following order.
1. Configuration of Auricle-Worn Device
2. Body-Temperature Measurement by Auricle-Worn Device
 2-1. Configuration of Information Processing Unit
 2-2. Eardrum Recognition Process
 (1) Eardrum Temperature Processing Apparatus that Performs Eardrum Recognition Process Using Captured Image
  (1-A) Configuration of Eardrum Temperature Processing Apparatus
  (1-B) Temperature Measurement Process by Eardrum Temperature Processing Apparatus
  (1-C) Correction of Measured Temperature
 (2) Eardrum Temperature Processing Apparatus that Performs Eardrum Recognition Process Using Thermal Image
  (2-A) Configuration of Eardrum Temperature Processing Apparatus
  (2-B) Temperature Measurement Process by Eardrum Temperature Processing Apparatus
3. Hardware Configuration Example <1. Configuration of Auricle-Worn Device>

Figure 2:
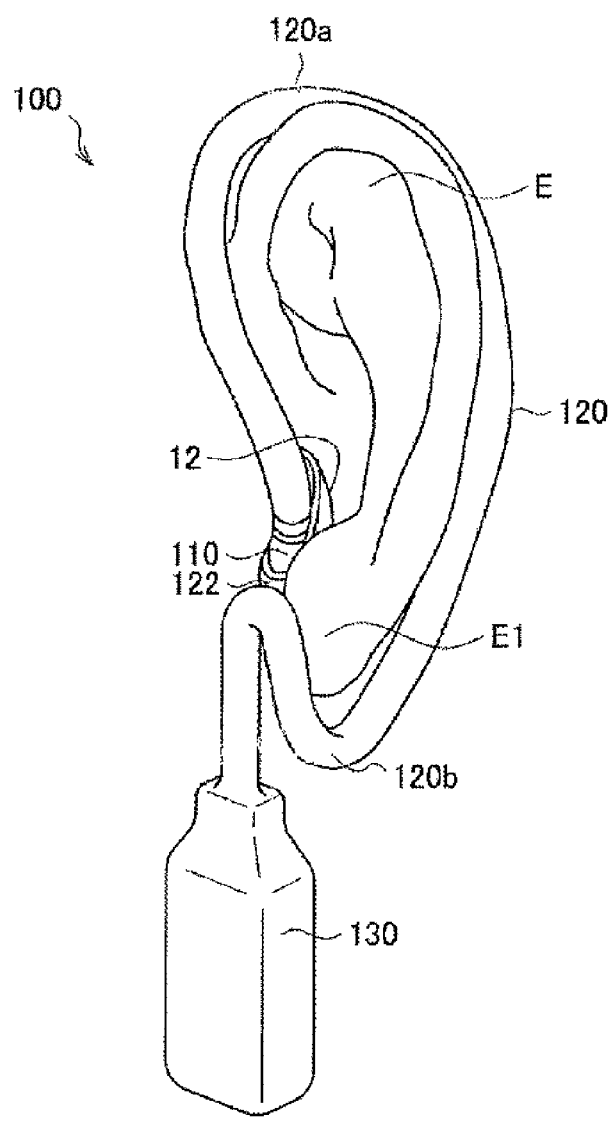
FIG. 2 is an explanatory diagram illustrating a state in which the auricle-worn device illustrated in FIG. 1 has been attached to a user's ear.
Figure 3:
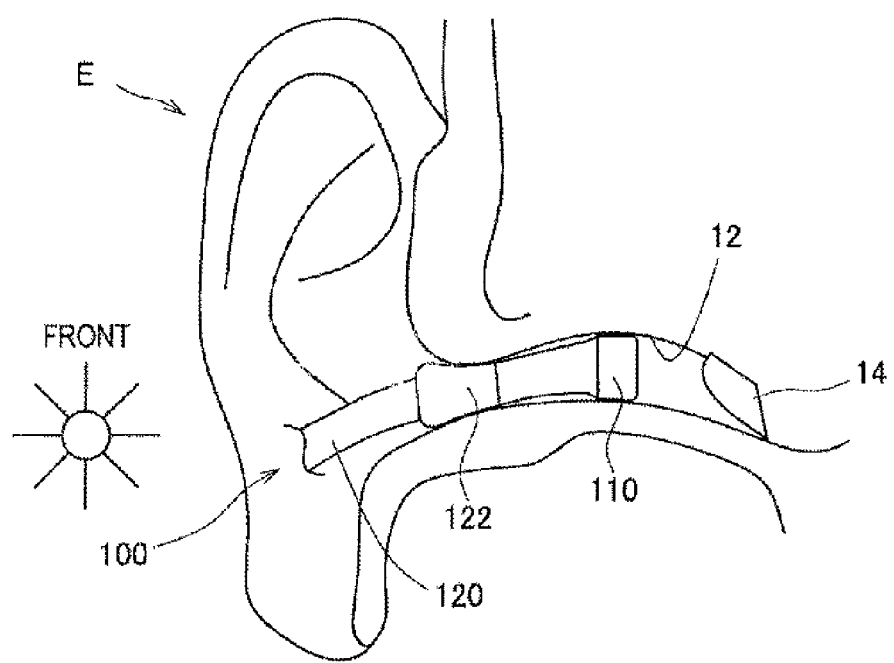
FIG. 3 is an explanatory diagram illustrating a state of an inside of an external ear canal when the auricle-worn device has been attached.
Figure 4:
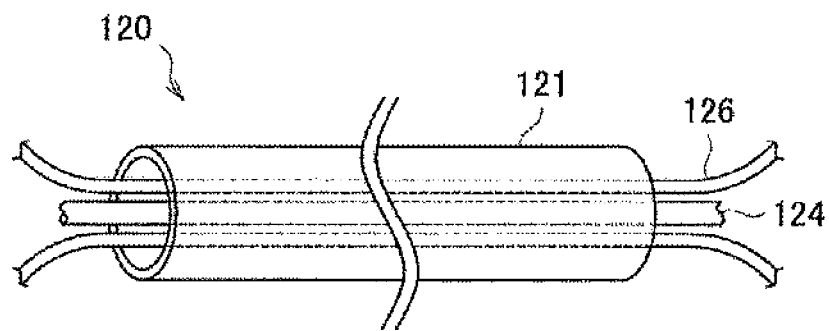
FIG. 4 is a partially enlarged diagram illustrating a configuration example of a main body unit.
Figure 5:
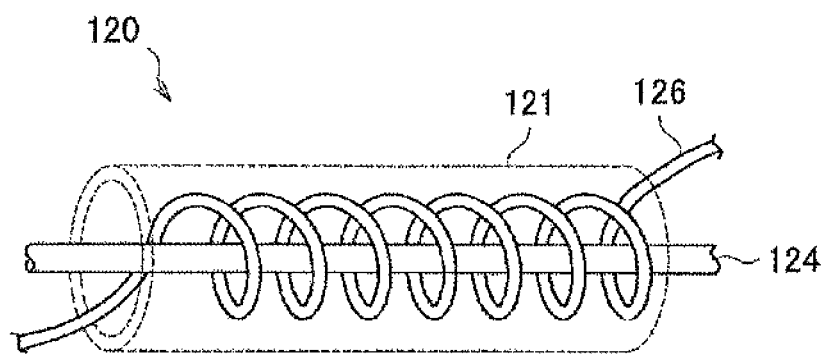
FIG. 5 is a partially enlarged diagram illustrating another configuration example of the main body unit.

First, the configuration of the auricle-worn device 100 having an information processing apparatus that measures an eardrum temperature in accordance with an embodiment of the present disclosure will be described with reference to FIGS. 1 to 5. FIG. 1 is an external appearance diagram illustrating the configuration of the auricle-worn device 100 in accordance with this embodiment. FIG. 2 is an explanatory diagram illustrating a state in which the auricle-worn device 100 illustrated in FIG. 1 has been attached to a user's ear. FIG. 3 is an explanatory diagram illustrating a state of an inside of an external ear canal when the auricle-worn device 100 has been attached. FIG. 4 is a partially enlarged diagram illustrating a configuration example of a main body unit 120. FIG. 5 is a partially enlarged diagram illustrating another configuration example of the main body unit 120.

The auricle-worn device 100 in accordance with this embodiment is a non-contact thermometer for measuring a deep body temperature by detecting an eardrum temperature of the user's eardrum. For example, as illustrated in FIG. 1, the auricle-worn device 100 includes a temperature sensor unit 110 that detects the eardrum temperature, the main body unit 120, and an information processing unit 130 that performs temperature processing.

The temperature sensor unit 110 is a detection unit that detects the eardrum temperature in a non-contact form. For example, a pyroelectric infrared sensor can be used as the temperature sensor unit 110. The temperature sensor unit 110 is inserted into an external ear canal 12 of the user as illustrated in FIG. 2, and detects infrared rays radiated from the eardrum. Therefore, the temperature sensor unit 110 outputs the detection result as an electric signal to the information processing unit 130 via a wiring arranged within the main body unit 120. An earpiece 122 for holding the temperature sensor unit 110 inside the external ear canal 12 is provided in a connection portion between the temperature sensor unit 110 and the main body unit 120. The earpiece 122 is formed of a material such as a silicone resin.

The main body unit 120 is an attachment member for holding a state in which the temperature sensor unit 110 has been inserted into the external ear canal 12 of the user. As illustrated in FIG. 1, the main body unit 120 has one end connected to the temperature sensor unit 110 and the other end connected to the information processing unit 130. In an intermediate portion that connects the temperature sensor unit 110 and the information processing unit 130, a first bent portion 120a to be attached to an upper part of an auricle E of the user and a second bent portion 120b to be attached to an earlobe E1 at a lower part of the auricle E of the user are formed in correspondence with an ear shape. When the auricle-worn device 100 is attached as illustrated in FIG. 2, the temperature sensor unit 110 is in a state in which the temperature sensor unit 110 faces an eardrum 14 within the external ear canal 12 as illustrated in FIG. 3. This state is held by the earpiece 122 around an opening of the external ear canal 12.

In addition, a wiring that transfers the detection result by the temperature sensor unit 110 to the information processing unit 130 is provided inside the main body unit 120. An internal structure of the main body unit 120 is illustrated in FIGS.

4 and 5. The main body unit 120 is formed of a plastically deformable shape-retaining material.

For example, as illustrated in FIG. 4, the main body unit 120 can include a cylindrical cover 121 formed of an elastic material such as a silicone resin, and one wire 124 and a wiring 126 provided inside the cover 121. The wire 124 can be provided to hold the shape of the main body unit 120, and the main body unit 120 can be aligned on the shape of the ear by deforming the shape of the wire 124. The wiring 126 is a cable through which a signal flows by connecting the temperature sensor unit 110 and the information processing unit 130, and is provided in a longitudinal direction of the cover 121 along with the wire 124 as illustrated in FIG. 4. As described above, it is possible to implement the lightweight auricle-worn device 100 by simplifying the configuration of the main body unit 120.

Alternatively, as illustrated in FIG. 5, the wiring 126 may be wound around the wire 124. Thereby, it is possible to prevent the wiring 126 from being disconnected when the shape of the main body unit 120 is changed. At this time, all or only part of the wiring 126 may be wound over the temperature sensor unit 110 to the information processing unit 130.

The information processing unit 130 is a functional unit that calculates the eardrum temperature based on the detection result of the temperature sensor unit 110, and is connected to the other end of the main body unit 120 and arranged on a lower part of the earlobe E1 as illustrated in FIG. 2. The information processing unit 130 includes an electronic circuit board or the like, and performs a process of converting an electric signal output from the temperature sensor unit 110 via the wiring 126 into a measured value of the body temperature of the user or the like. In addition, the information processing unit 130 in accordance with this embodiment also executes an eardrum recognition process of recognizing a position of the eardrum 14 based on image information. It is possible to precisely measure the eardrum temperature by performing the eardrum recognition process.

For the attachment of the above-described auricle-worn device 100, first, the main body unit 120 is deformed so that the temperature sensor unit 110 is easily attached to the auricle E. By loosely bending the first bent portion 120a and the second bent portion 120b, it is possible to extend a linear distance between both ends of the main body unit 120 and it is easy to attach the main body unit 120 to the auricle E. In addition, it is also possible to extend the distance between the first bent portion 120a and the second bent portion 120b so that the distance is greater than or equal to a distance from an upper end of the auricle E to a lower end of the earlobe E1. In this case, the first bent portion 120a and the second bent portion 120b can maintain a deformed bent shape.

Then, the temperature sensor unit 110 is inserted into the external ear canal 12, and the earpiece 122 is arranged around the opening of the external ear canal 12. In this state, the main body unit 120 is deformed and adjusted so that the main body unit 120 is aligned on the auricle E of the user, and the auricle-worn device 100 is attached. For example, the auricle-worn device 100 can be stably attached to the auricle E by narrowing the extended distance between the first bent portion 120a and the second bent portion 120b to the distance from the upper end of the auricle E to the lower end of the earlobe E1. In addition, the bent shape of the first bent portion 120a may be formed to be placed on the auricle E and the bent shape of the second bent portion 120b may be deformed to lightly pinch the auricle E of the user. In this case, the first bent portion 120a and the second bent portion 120b can maintain their bent shapes.

As described above, the auricle-worn device 100 can maintain the attachment state without applying a pressure around the auricle E of the user. In addition, because the first bent portion 120a is placed on the auricle E of the user, and the second bent portion 120b is further attached to sandwich the earlobe E1, detachment from the auricle E can be prevented and the body temperature can be stably measured even when a direction of external force to the auricle-worn device 100 is not constant. Further, because the lightweight auricle-worn device 100 can be configured, it is possible to reduce a burden imposed on the user even in the attachment for a long time. Accordingly, the auricle-worn device 100 can be used even for body-temperature measurement under a condition that external force from many directions is loaded for a long time, for example, such as body-temperature measurement during activity or during sleep.

<2. Body-Temperature Measurement by Auricle-Worn Device>

The auricle-worn device 100 in accordance with this embodiment acquires a position of the eardrum 14 and a temperature inside the external ear canal 12 including the eardrum 14 as eardrum information by inserting the temperature sensor unit 110 into the external ear canal 12 and causing the temperature sensor unit 110 to face the eardrum 14. Therefore, the information processing unit 130 calculates an eardrum temperature based on the eardrum information acquired by the temperature sensor unit 110. Hereinafter, a body-temperature measurement method by the auricle-worn device 100 in accordance with this embodiment will be described based on FIGS. 6 to 21.

[2-1. Configuration of Information Processing Unit]

Figure 6:
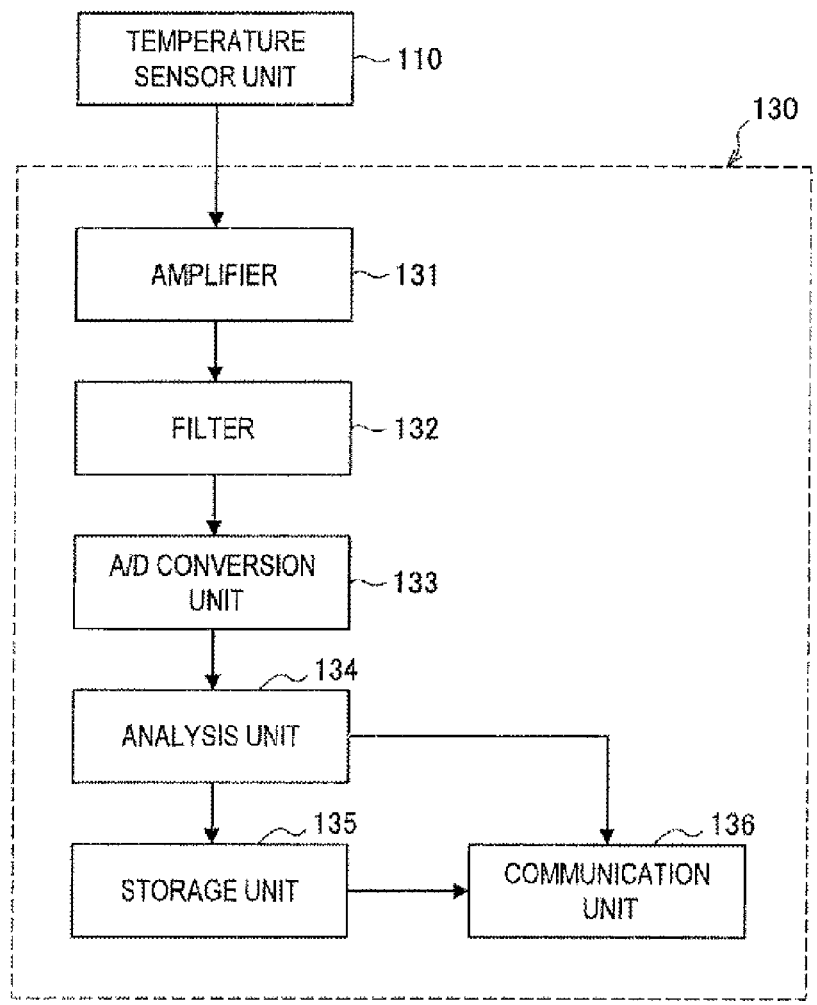
FIG. 6 is a block diagram illustrating a configuration of an information processing unit in accordance with the same embodiment.

First, the configuration of the information processing unit 130 in accordance with this embodiment will be described based on FIG. 6. FIG. 6 is a block diagram illustrating the configuration of the information processing unit 130 in accordance with this embodiment. As illustrated in FIG. 6, the information processing unit 130 includes an amplifier 131, a filter 132, an analog-to-digital (A/D) conversion unit 133, an analysis unit 134, a storage unit 135, and a communication unit 136.

The amplifier 131 amplifies an electric signal transmitted from the temperature sensor unit 110, and outputs the amplified electric signal to the filter 132. The filter 132 corrects the amplified electric signal by removing a predetermined band of noise from the amplified electric signal, and outputs the corrected electric signal to the A/D conversion unit 133. The A/D conversion unit 133 converts the electric signal from an analog signal into a digital signal, and outputs the digital signal to the analysis unit 134. The analysis unit 134 is a processing unit that determines a measured temperature by analyzing the digital signal, and can include an integrated circuit. The measured temperature determined by the analysis unit 134 is transmitted to at least one of the storage unit 135 and the communication unit 136.

The communication unit 136 outputs the measured temperature determined by the analysis unit 134 to an external device (not illustrated) such as a computer. A communication form of the communication unit 136 may be wireless communication or wired communication. When the wireless communication is performed, for example, it is possible to transmit a measurement result of a body temperature to a computer or the like while the user wears the auricle-worn device 100. In addition, when the wired communication is performed, for example, the measurement result is stored in the storage unit 135. After the end of the measurement, the auricle-worn device 100 is removed from the auricle and connected to the computer or the like by a cable or the like, and the measurement result stored in the storage unit 135 can be transmitted to the computer or the like. Specifically, there is a universal serial bus (USB), a wireless local area network (LAN), ZigBee (registered trademark), Bluetooth (registered trademark), or the like.

As described above, the auricle-worn device 100 measures the eardrum temperature of the user. In addition, because the auricle-worn device 100 can maintain its attachment state without pressing against the auricle E of the user even in the attachment for a long time, for example, it is possible to measure a body temperature at fixed intervals while the auricle-worn device 100 is attached for a long time, and perform analysis of daily fluctuation in the body temperature.

A display unit (not illustrated) connected to the communication unit 136 is further provided in the auricle-worn device 100, and hence the auricle-worn device 100 can cause the display unit to display the obtained measured temperature. Further, the auricle-worn device 100 may include a battery that supplies power to the information processing unit 130 and the like. When the display unit, the battery, and the like are provided in the auricle-worn device 100, arrangement positions thereof are not particularly limited. For example, the battery and the display unit may be connected to the other end of the main body unit 120 along with the information processing unit 130. The display unit and the battery may be provided between the first bent portion 120a and the second bent portion 120b.

[2-2. Eardrum Recognition Process]

Next, the configuration of the temperature sensor unit 110 will be described. It is necessary to accurately direct the temperature sensor unit 110 of the auricle-worn device 100 toward the eardrum 14 so as to continuously measure the eardrum temperature of the user accurately for a long time using the auricle-worn device 100.

There is a small temperature difference between the external ear canal 12 and the eardrum 14. The temperature of the normal eardrum 14 is set to be higher and a peak of the eardrum 14 measured by the temperature sensor unit 110 is set as the temperature of the eardrum 14. Therefore, the auricle-worn device 100 in accordance with this embodiment performs the eardrum recognition process of recognizing that the temperature sensor unit 110 accurately faces the eardrum 14, and measures the eardrum temperature. Thereby, it is possible to measure the eardrum temperature with a higher precision than in the related art.

Hereinafter, an eardrum temperature processing apparatus (information processing apparatus) that performs an eardrum recognition process provided in the auricle-worn device 100 in accordance with this embodiment and measures the eardrum temperature will be described. The eardrum temperature processing apparatus recognizes a position of the eardrum 14 and a temperature inside the ear canal including the eardrum from image information regarding the eardrum acquired by the temperature sensor unit 110 and calculates the eardrum temperature based on the above-described information. The eardrum temperature processing apparatus is the information processing apparatus provided in the auricle-worn device 100, and can include the temperature sensor unit 110 of the auricle-worn device 100, the wiring 126, and the information processing unit 130 described above. In addition, although an example of the eardrum temperature processing apparatus shown hereinafter fully provided in the auricle-worn device 100 will be described, the present technology is not limited thereto. Some functions can also be provided in an external device communicable with the auricle-worn device 100.

For example, an example of image information regarding the eardrum to be analyzed by the eardrum temperature processing apparatus is a captured image, a thermal image, or the like. Therefore, eardrum recognition processes when the captured image is used and when the thermal image is used will be described hereinafter.

Figure 7:
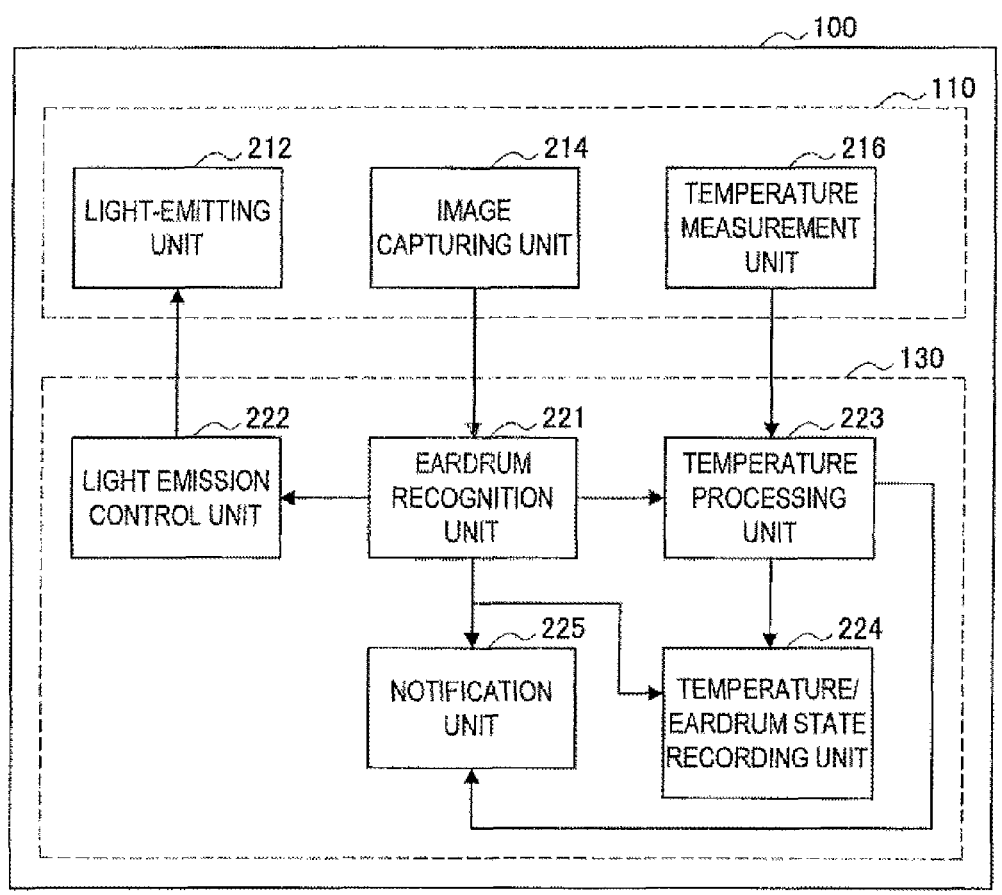
FIG. 7 is a block diagram illustrating a configuration of an eardrum temperature processing apparatus that performs an eardrum recognition process using a captured image.

(1) Eardrum Temperature Processing Apparatus that Performs Eardrum Recognition Process Using Captured Image (1-A) Configuration of Eardrum Temperature Processing Apparatus First, the configuration of the eardrum temperature processing apparatus that performs the eardrum recognition process using the captured image will be described based on FIG. 7. FIG. 7 is a block diagram illustrating the configuration of the eardrum temperature processing apparatus that performs the eardrum recognition process using the captured image.

For the eardrum temperature processing apparatus, which is provided in the auricle-worn device 100 and performs the eardrum recognition process using the captured image, a light-emitting unit 212, an image capturing unit 214, and a temperature measurement unit 216 are first provided in the temperature sensor unit 110 as illustrated in FIG. 7. The light-emitting unit 212 is a light-emitting element that emits light based on an instruction from the information processing unit 130. For example, a light-emitting diode (LED) or the like can be used as the light-emitting unit 212. The image capturing unit 214 is an imaging element that captures image information including the eardrum 14. For example, a complementary metal oxide semiconductor (CMOS) image sensor or the like can be used as the image capturing unit 214. The image capturing unit 214 performs imaging based on an instruction from the information processing unit 130, and outputs an acquired image to the information processing unit 130. The temperature measurement unit 216 is a measurement unit that measures a temperature inside the auricle including the eardrum 14. For example, a thermal infrared sensor such as a thermopile using thermal electromotive force or a thermistor using a temperature change in electrical resistance can be used. Temperature information measured by the temperature measurement unit 216 is output to the information processing unit 130.

Figure 8:
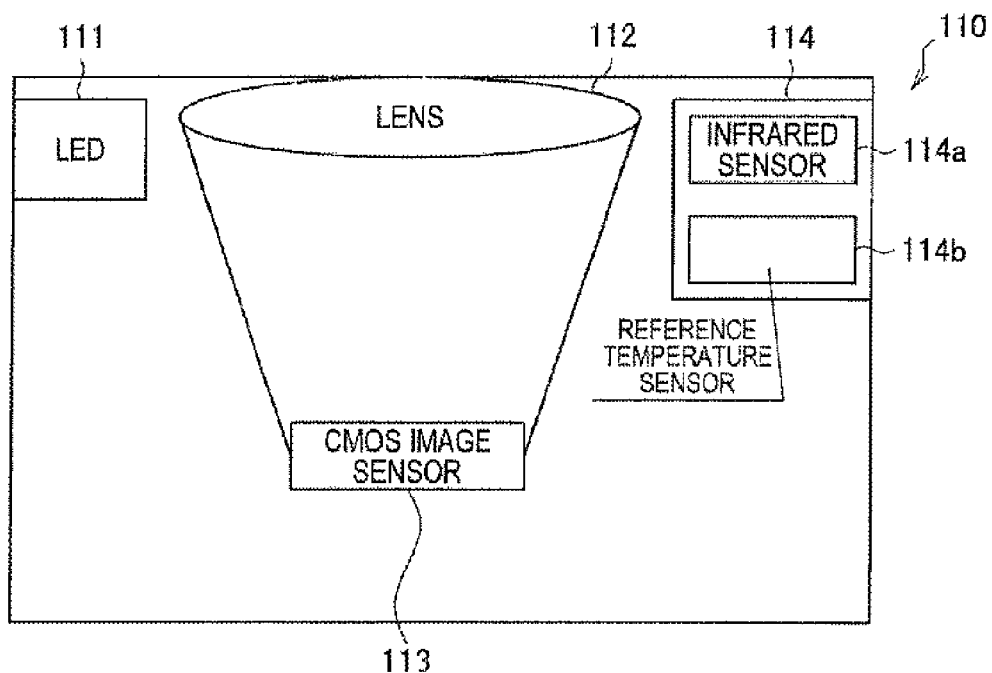
FIG. 8 is an explanatory diagram illustrating a specific configuration example of a temperature sensor unit.

Here, a specific configuration example of the temperature sensor unit 110 will be described based on FIGS. 8 to 10. For the temperature sensor unit 110, for example, as illustrated in FIG. 8, an LED 111 is provided as the light-emitting unit 212 at its tip end. The LED 111 is arranged to emit light to the eardrum 14, and emits light based on an instruction of the information processing unit 130. In addition, as the image capturing unit 214, a lens 112 and a CMOS image sensor 113 are provided. For light reflected by the external ear canal 12 or the eardrum 14 according to light emitting of the LED 111, an image is formed on the CMOS image sensor 113 via the lens 112 and output to the information processing unit 130. Further, as the temperature measurement unit 216, a radiation thermometer 114 including an infrared sensor 114a, which measures a temperature difference by receiving infrared rays emitted from an object, and a reference temperature sensor 114b, which measures an absolute temperature of a measuring instrument, is provided. For example, a thermopile or the like can be used as the infrared sensor 114a. For example, a thermistor or the like can be used as the reference temperature sensor 114b. Infrared-domain light detected by the radiation thermometer 114 is converted into an electric signal, and the electric signal is output to the information processing unit 130.

Figure 9:
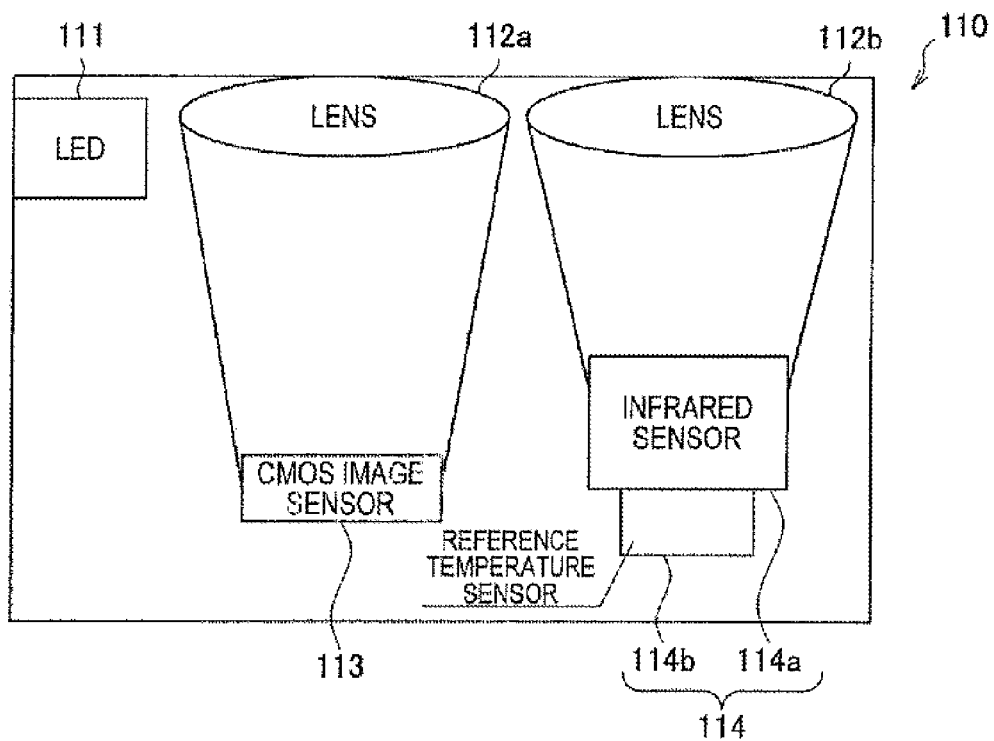
FIG. 9 is an explanatory diagram illustrating another specific configuration example of the temperature sensor unit.

As another configuration example of the temperature sensor unit 110, for example, as illustrated in FIG. 9, a lens 112b for forming an image of infrared-domain light on the radiation thermometer 114, which is the temperature measurement unit 216, may be provided in addition to a lens 112a and the CMOS image sensor 113, in the temperature sensor unit 110. Thereby, the temperature measurement unit 216 can more reliably receive the infrared-domain light.

Figure 10:
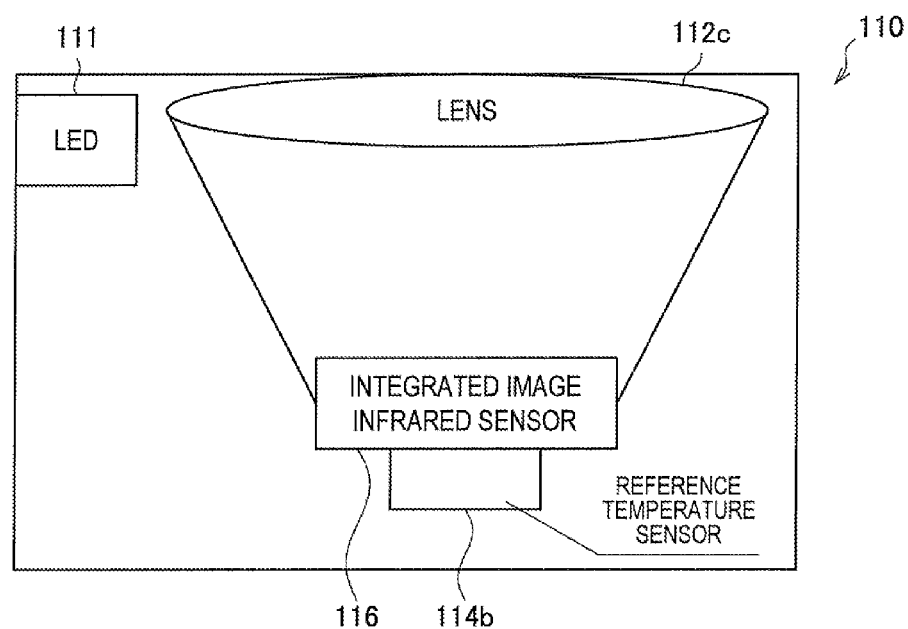
FIG. 10 is an explanatory diagram illustrating another specific configuration example of the temperature sensor unit.

As still another configuration example of the temperature sensor unit 110, for example, as illustrated in FIG. 10, the image capturing unit 214 and the temperature measurement unit 216 may be configured using an integrated image infrared sensor 116 in which a CMOS image sensor and an infrared sensor are integrally formed and a reference temperature sensor 114b. Thereby, the number of components constituting the temperature sensor unit 110 can be reduced.

Returning to the description of FIG. 7, the information processing unit 130 includes an eardrum recognition unit 221, a light emission control unit 222, a temperature processing unit 223, a temperature/eardrum state recording unit 224, and a notification unit 225. The eardrum recognition unit 221 determines whether A tip end of the temperature sensor unit 110 faces the eardrum 14, and controls each functional unit based on the determination result. The eardrum recognition unit 221 acquires image information including the eardrum 14, and recognizes a position of the eardrum 14. When the temperature sensor unit 110 has been inserted into the external ear canal 12, the eardrum recognition unit 221 instructs the light emission control unit 222 to cause the light-emitting unit 212 to emit light based on an input of a temperature measurement instruction from the user. In addition, the eardrum recognition unit 221 acquires an image captured by the image capturing unit 214 as image information according to light emitting of the light-emitting unit 212, and analyzes a position of the eardrum 14. When the image information is accurately acquired, the eardrum recognition unit 221 instructs the light emission control unit 222 to turn off the light-emitting unit 212.

The eardrum recognition unit 221 further performs an image recognition process on the acquired image information, and calculates a rate occupied by the eardrum 14 (an eardrum occupancy rate) in the image. Therefore, the eardrum recognition unit 221 outputs the calculated eardrum occupancy rate to the temperature processing unit 223 and at least one of the temperature/eardrum state recording unit 224 and the notification unit 225.

The light emission control unit 222 controls the light emitting of the light-emitting unit 212. The light emission control unit 222 causes the light-emitting unit 212 to emit light based on a light emission instruction from the eardrum recognition unit 221 and turns off the light-emitting unit 212 based on a turn-off instruction.

The temperature processing unit 223 determines an eardrum temperature of the eardrum 14 based on a temperature measured by the temperature measurement unit 216 and the recognition result of the eardrum recognition unit 221. The temperature processing unit 223 determines that the temperature sensor unit 110 faces the eardrum 14 when the eardrum occupancy rate calculated by the eardrum recognition unit 221 is greater than or equal to a predetermined value, and determines that the measured temperature of the temperature measurement unit 216 is reliable. At this time, the temperature processing unit 223 determines the measured temperature as the eardrum temperature. The eardrum temperature is output to at least one of the temperature/eardrum state recording unit 224 and the notification unit 225.

The temperature/eardrum state recording unit 224 is a storage unit that records the eardrum determination result detected by the eardrum recognition unit 221 and the eardrum temperature measured by the temperature measurement unit 216 in a storage unit (not illustrated). The storage unit may be a memory or the like provided in the eardrum recognition processing apparatus or a memory card or the like attachable to or detachable from the eardrum recognition processing apparatus. The eardrum determination result and the eardrum temperature recorded by temperature/eardrum state recording unit 224, for example, are used to determine the validity/invalidity of the temperature measurement result.

The notification unit 225 notifies the user of a position state of the temperature sensor unit 110, which is a temperature measurement unit for the eardrum 14, that is, whether the tip end of the temperature sensor unit 110 faces the eardrum 14, based on the detection result of the eardrum recognition unit 221. The notification unit 225, for example, may provide notification by sound or the like when the tip end of the temperature sensor unit 110 does not face the eardrum 14, and provide notification by sound or the like when the tip end of the temperature sensor unit 110 faces the eardrum 14. Alternatively, by outputting different sounds when the tip end of the temperature sensor unit 110 does not face the eardrum 14 and when the tip end of the temperature sensor unit 110 faces the eardrum 14, notification of whether the temperature sensor unit 110 faces the eardrum 14 may be provided. In addition, the notification unit 225 notifies the user of the eardrum temperature determined by the temperature processing unit 223.

Figure 11:
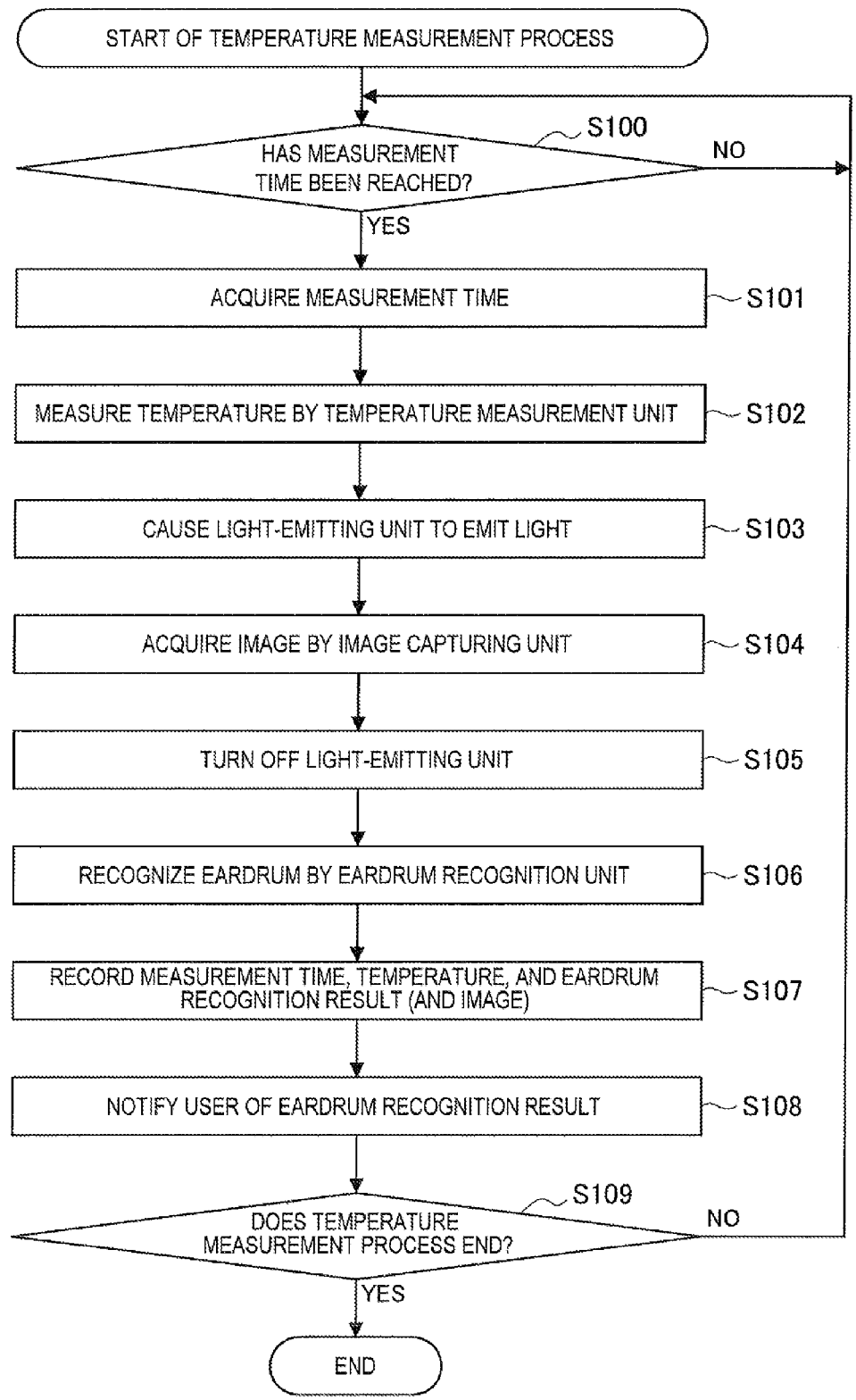
FIG. 11 is a flowchart illustrating a temperature measurement process by the eardrum temperature processing apparatus in accordance with the same embodiment.

(1-B) Temperature Measurement Process by Eardrum Temperature Processing Apparatus The temperature measurement process by the eardrum temperature processing apparatus illustrated in FIG. 7 will be described based on FIG. 11. FIG. 11 is a flowchart illustrating the temperature measurement process by the eardrum temperature processing apparatus in accordance with the same embodiment.

The temperature measurement process by the eardrum temperature processing apparatus is started when a measurement time has been reached as illustrated in FIG. 11 (S100). The measurement time, for example, such as every second, every minute, or a designated time set by the user, can be arbitrarily set. The eardrum recognition unit 221 iteratively executes the process of step S100 when the measurement time has not been reached. When reaching a measurement time, the measurement time is acquired (S101), and thereafter, the temperature measurement unit 216 first measures a temperature within the external ear canal 12 (S102). The temperature measured in step S102 becomes the temperature (eardrum temperature) of the eardrum 14. In this embodiment, the following eardrum recognition process is performed. When the temperature sensor unit 110 accurately faces the eardrum 14, the measured temperature is determined to be the eardrum temperature. Thereby, it is possible to accurately measure the eardrum temperature.

Then, in order to perform the eardrum recognition process, the eardrum recognition unit 221 instructs the light emission control unit 222 to cause the light-emitting unit 212 to emit light. The light emission control unit 222 causes the light-emitting unit 212 to emit the light by receiving the light emission instruction (S103). When the light-emitting unit 212 emits the light, the image capturing unit 214 acquires an image of the eardrum 14 (S104), and outputs the acquired image to the eardrum recognition unit 221. Upon receipt of an input of the image of the eardrum 14, the eardrum recognition unit 221 instructs the light emission control unit 222 to turn off the light-emitting unit 212, and the light-emitting unit 212 is turned off (S105). Because there is a concern that the temperature within the external ear canal 12 is likely to rise while the light-emitting unit 212 emits the light and the eardrum temperature is not accurately measureable, the light-emitting unit 212 may be turned off except for when the measurement is performed.

Figure 12:
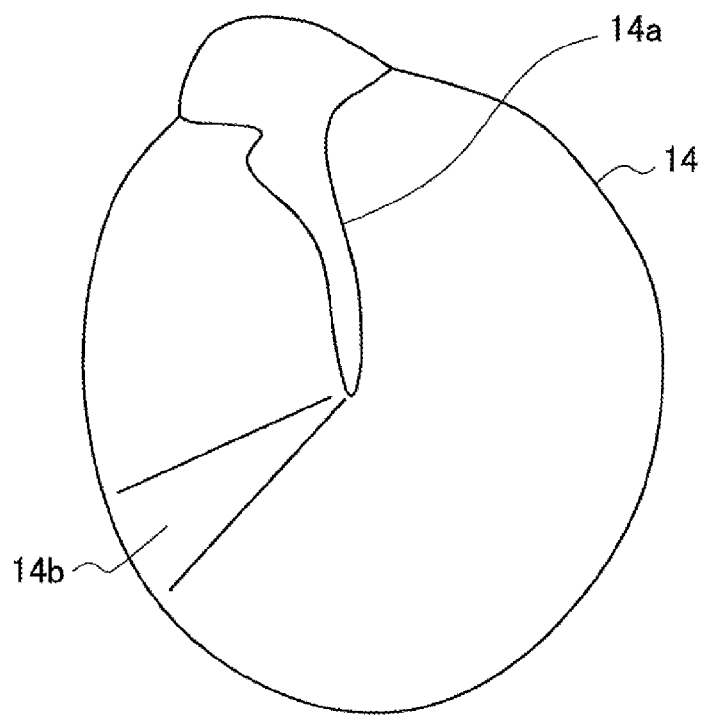
FIG. 12 is an explanatory diagram illustrating an example of a captured image of an eardrum.

When the captured image of the eardrum 14 is acquired in the process of steps S103 to S105, the eardrum recognition unit 221 performs the eardrum recognition process based on the image (S106). In the eardrum recognition process, a position of the eardrum 14 is specified by recognizing a light cone from the image obtained by capturing the eardrum 14. An example of the captured image of the eardrum 14 is illustrated in FIG. 12. When the eardrum 14 is imaged, a malleus 14a and a light cone 14b are characteristically viewed. The malleus 14a is a bone attached closely to the inside of the eardrum 14, and is viewed simultaneously when the eardrum 14 is viewed. The light cone 14b is viewed when light emitted by the light-emitting unit 212 is reflected on the eardrum 14 in the ear. The eardrum recognition unit 221 specifies a position of the eardrum within the captured image by recognizing the above-described feature.

An example of an image recognition algorithm for use in the eardrum recognition process is a technique of boosting and learning a pixel difference feature (Japanese Patent No. 4517633). Further, a technique using a Gabor filter in a filter base (Japanese Patent No. 4333364), a technique using a Haar-like feature, or the like is also applicable to the eardrum recognition process.

In these techniques, an eardrum image, an image in which only part (for example, a half) of the eardrum is shown, an image in which only the external ear canal is shown, and the like are collected in a large volume. A designer of the eardrum temperature processing apparatus labels the images one by one by cutting the image into a part which is the eardrum 14 and a part which is not the eardrum 14. The labeling is performed in the following order.

Procedure 1: Collection of Images

First, a captured image of the inside of the external ear canal is collected. In this case, it is desirable to perform imaging using a lens having an angle of view equivalent to that of a lens used in the radiation thermometer 114. Various images including an image in which the front of the eardrum 14 is clearly shown, an image in which the eardrum 14 is obliquely shown, an image in which no eardrum 14 is shown, and the like are captured and collected.

Procedure 2: Determination of Eardrum Region (Labeling)

A human determines whether a region (eardrum region) of the eardrum 14 is shown or not shown in the image collected in Procedure 1. When the eardrum is shown in the image, the human encloses the eardrum region in the rectangle. Further, when the malleus 14a is viewed, an angle of the malleus 14a is measured. Alternatively, a straight line may be drawn along the malleus 14a. This is because the eardrum region and the angle of the malleus 14a within the image become important information as teacher data of machine learning.

For the image in which the eardrum 14 is shown on the occasion of labeling, the image may be rotated and normalized so that the direction of the malleus 14a is aligned in a fixed direction (for example, in a vertical direction as illustrated in FIG. 12). Thereby, a feature quantity is likely to be produced and a strong classifier can be created.

Figure 13:
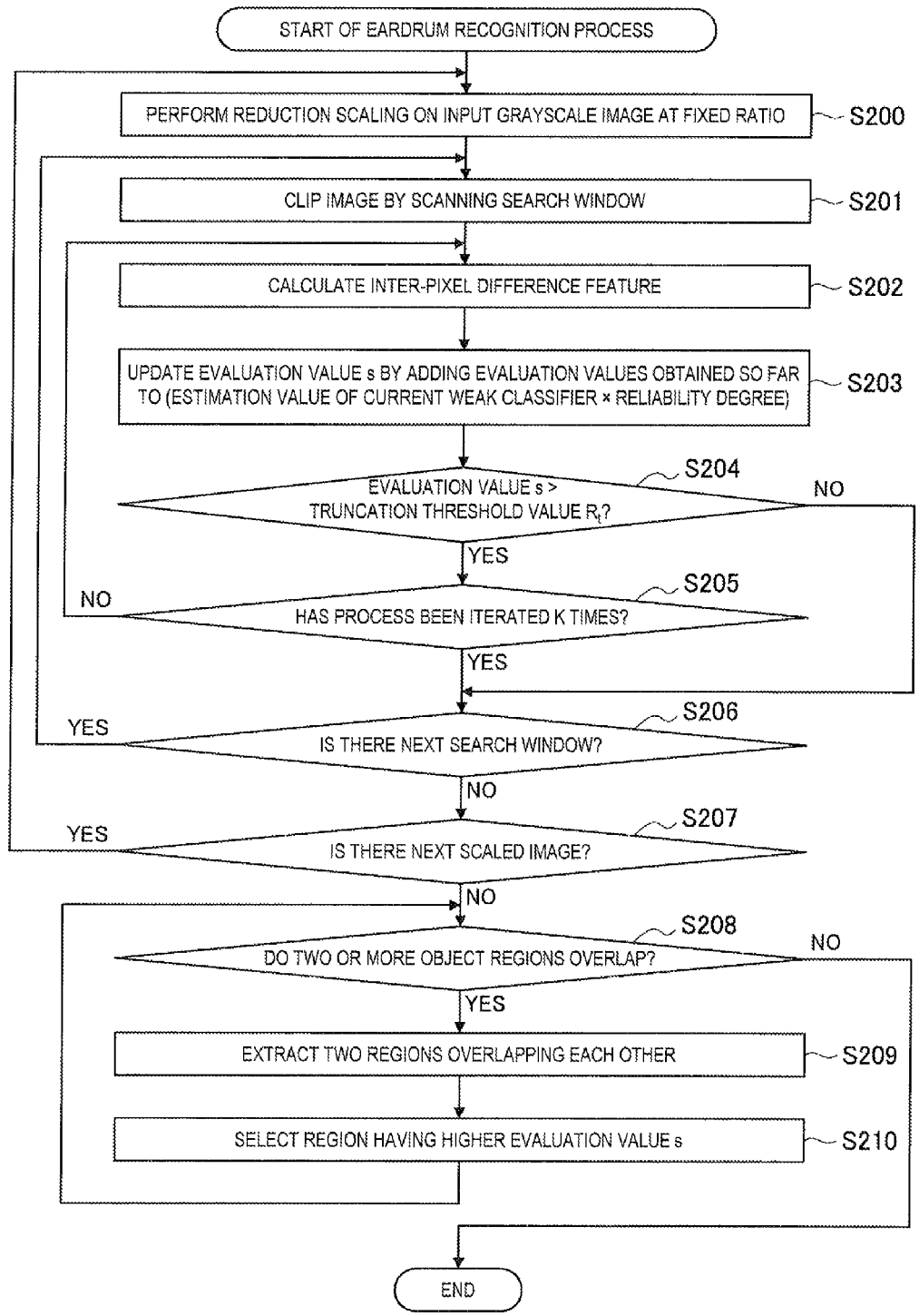
FIG. 13 is a flowchart illustrating an example of the eardrum recognition process.

Here, an example of the eardrum recognition process of step S106 will be described in detail based on FIG. 13. FIG. 13 is a flowchart illustrating the example of the eardrum recognition process to which an object detection process disclosed in Japanese Unexamined Patent Application Publication No. 2005-157679 has been applied. The eardrum 14 serves as an object. In this case, the eardrum recognition unit 221 functions as a scaling unit that performs scaling by enlarging or reducing a grayscale image, which is an input image, and a scanning unit that sequentially scans the scaled input image in a size of a predetermined-size window image. Further, the eardrum recognition unit 221 functions as a classifier that classifies whether each window image sequentially scanned by the scanning unit is an object or a non-object. That is, the eardrum recognition unit 221 generates scaled images by enlarging or reducing the input image to all designated scales, clips a window image by sequentially scanning a window having a size of an object desired to be detected, and classifies whether the clipped image is an object.

According to a detailed description, first, the eardrum recognition unit 221 scales an image captured by the image capturing unit 214 at a fixed ratio (S200). The image processed by the eardrum recognition unit 221 is a grayscale image. The timing at which the scaled image is generated is set as a point in time at which eardrum detection from the entire region of a previous output scaled image has ended. The process moves to processing on an input image of the next frame at a point in time at which the scaled image is smaller than a window image. When the scaled image is generated, the eardrum recognition unit 221 clips a window image by scanning a position of a search window in length and width for the scaled image (S201).

Then, the eardrum recognition unit 221 determines whether the window image clipped in step S201 is an object, that is, the eardrum 14. The eardrum recognition unit 221 calculates a value (an updated value of a weighted majority decision value) obtained by sequentially weighting and adding estimation values f(x) of a plurality of weak classifiers for the window image as an evaluation value s. It is determined whether the window image is the object and whether the classification is truncated based on the evaluation value s.

That is, when the window image is input, the eardrum recognition unit 221 initializes its evaluation value to s=0, and calculates an inter-pixel difference feature $d_t$ (S202). The inter-pixel difference feature $d_t$ is a difference between luminance values $I_1$ and $I_2$ of two arbitrary pixels, and is expressed by the following Expression (1). The pixel luminance value I is expressed by the following Expression (2). (x, y) represents a position of a pixel constituting an image.

$$d_t = I_1 - I_2 \qquad (1)$$

$$I(x, y) = \sum_{x' < x, y' < y} S(x', y') \qquad (2)$$

The eardrum recognition unit 221 further reflects an estimation value of whether the window image is the object in the evaluation value s for determining whether the window image is the object (S203). Therefore, the eardrum recognition unit 221 determines whether the evaluation value s is greater than a truncation threshold value $R_t$ for truncation in mid-course of detection in a classification process (S204). When the evaluation value s is greater than the truncation threshold value $R_t$, the eardrum recognition unit 221 determines whether the process has been iterated a predetermined number of times (K times) (S205). When the process has not been iterated a predetermined number of times (K times), the process from step S202 is iterated.

On the other hand, when it is determined that the process has been iterated a predetermined number of times (K times) in step S205 or when it is determined that the evaluation value s is less than the truncation threshold $R_t$ in step S204, the eardrum recognition unit 221 determines whether there is the next search window (S206). The eardrum recognition unit 221 determines whether the next search window is the object according to whether the acquired evaluation value s is greater than 0. When the next search window is the object, the eardrum recognition unit 221 stores a current window position, classifies whether there is the next search window, and iterates the process from step S201 when there is the next search window. On the other hand, when the search window has been scanned in all the next regions, the eardrum recognition unit 221 determines whether there is the next scaled image (S207).

When it is determined that there is the next scaled image in step S207, the eardrum recognition unit 221 iterates the process from step S200. The scaling process of step S200 ends at a point in time at which the scaled image is smaller than the window image. On the other hand, when it is determined that there is no next scaled image in step S207, the eardrum recognition unit 221 executes a process of deleting an overlapping region (S208 to S210). The process of deleting an overlapping region is a process of removing regions overlapping each other when a region determined to be a target physical object overlaps in one input image.

First, the eardrum recognition unit 221 determines whether there are regions overlapping each other (S208). Therefore, when there are a plurality of overlapping regions stored in step S205, the eardrum recognition unit 221 extracts two regions overlapping each other, deletes a region having a lower evaluation value s between the two regions by regarding the region as having a lower reliability degree, and selects a region having a higher evaluation value s (S210). Therefore, the process from step S208 is reiterated. Thereby, only one region having a highest evaluation value s is selected from among extracted regions overlapping a plurality of times. When two or more object regions do not overlap and when there is no object region, the process for one input image ends and the process moves to the next frame processing.

According to the above-described eardrum recognition process, an object is detected using a classifier that has learned from a weak classifier, which performs weak classification by an inter-pixel difference feature, according to group learning. Thus, a process of reading luminance values of two corresponding pixels in a window image and calculating a feature quantity of an object by merely calculating a difference therebetween ends. Because the eardrum recognition process can be performed at a very high speed, real-time eardrum recognition is possible.

In addition, the eardrum recognition unit 221 makes a comparison with the truncation threshold value $R_t$ every time the evaluation value s is sequentially updated by adding a value obtained by multiplying a classification result (estimation value) classified from the feature quantity by a reliability degree for the weak classifier used in the classification. At this time, the calculation of the weak classifier is truncated when the evaluation value s is less than the truncation threshold value $R_t$, and the eardrum recognition can be performed at a higher speed by moving the process to processing on the next window image and rapidly reducing an ineffective calculation.

That is, when window images have been clipped by scanning all regions of an input image, an image obtained by performing reduction scaling on the input image, and a scaled image, the window images are unlikely to be an object and most of the window images are a non-object. It is possible to extremely increase the efficiency of the classification process by truncating the classification of the window image, which is a non-object, in mid-course. On the other hand, when there are a large number of objects to be detected, a threshold value for truncating a calculation of a window image obviously determined to be an object in mid-course may be provided according to a technique similar to that of the above-described truncation threshold value. Further, it is possible to set a search window with an arbitrary size and detect an object with an arbitrary size by scaling the input image using the scaling unit.

In addition, when the eardrum recognition process is performed, it is possible to obtain a recognition result without depending upon an insertion direction of the temperature sensor unit 110 by rotating a capturing image by a fixed angle (for example, about 15 degrees) and making a determination by the eardrum recognition unit 221. Highly precise recognition is performed for eardrums with various sizes by performing scaling for enlarging or reducing an image to correspond to a large or small eardrum size in addition to the rotation and making a determination by the eardrum recognition unit 221.

In addition, a recognition process is possible, without performing rotation or scaling in advance, using a processing method using a scale invariant feature transform (SIFT) feature quantity, which is a rotation invariant feature quantity, a processing method of obtaining a luminance gradient of an image or creating a histogram discretized for every angle in each local region, or the like.

When position information regarding the eardrum 14 is acquired according to the eardrum recognition process, the eardrum recognition unit 221 calculates an eardrum occupancy rate, which is a ratio of a part in which the eardrum 14 is shown in a captured image. It is possible to determine whether the temperature sensor unit 110 substantially directly faces the eardrum 14 and temperature measurement is accurately performed from the eardrum occupancy rate. The eardrum recognition unit 221 outputs the calculated eardrum occupancy rate to the temperature processing unit 223. The temperature processing unit 223 determines the measured temperature of the temperature measurement unit 216 as the eardrum temperature when the eardrum occupancy rate is greater than or equal to a predetermined value.

In addition, the eardrum recognition unit 221 determines whether the temperature sensor unit 110 faces the eardrum 14 based on the eardrum occupancy rate, and allows the user to adjust the direction of the temperature sensor unit 110 when the temperature sensor unit 110 does not face the eardrum 14. Thus, the eardrum recognition unit 221 continuously recognizes the position of the eardrum 14. The recognition of the position of the eardrum 14 may be performed by executing the eardrum recognition process as described above or by tracking the position of the eardrum 14 recognized once. Because the eardrum recognition process is generally time-consuming, sight of the eardrum 14 is lost until the process is completed. Because a processing load of the tracking is lower than that of the eardrum recognition process, it is possible to specify the position of the eardrum 14 at a high speed and reduce power consumption.

Figure 14:
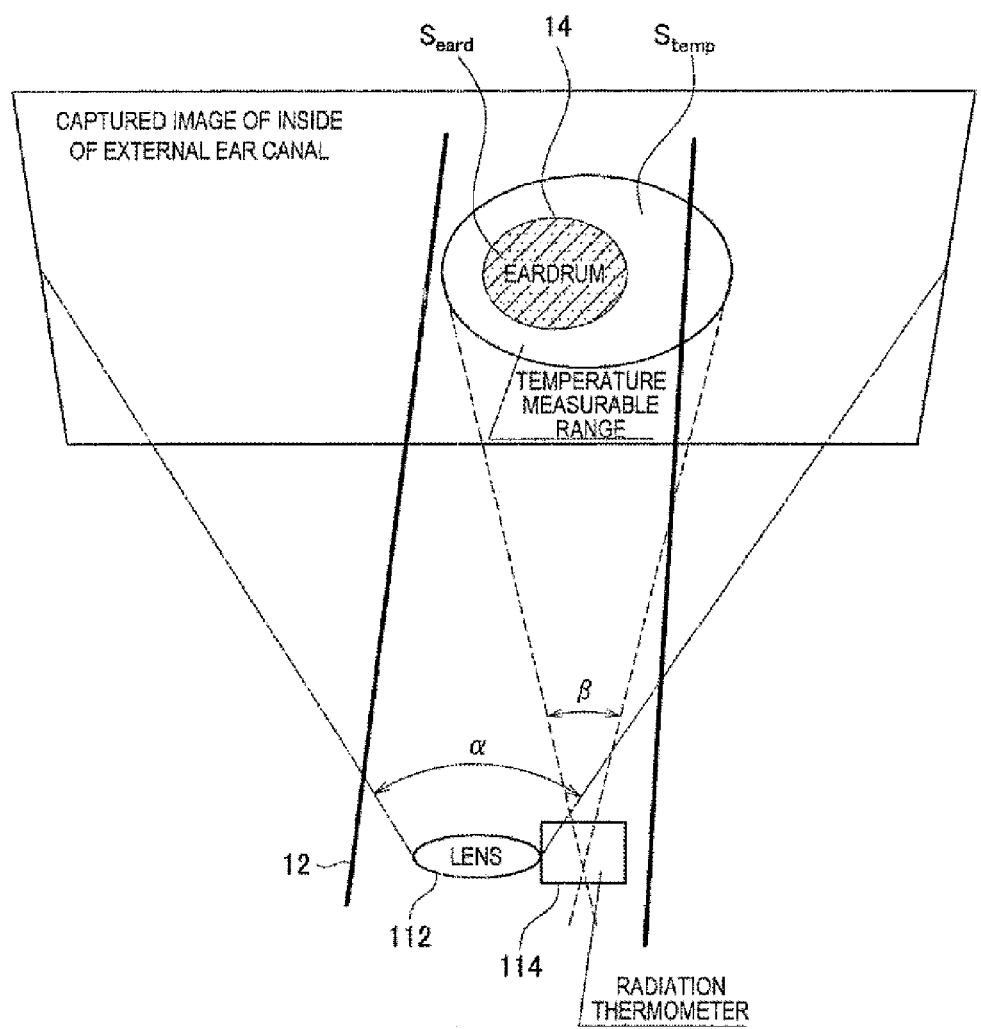
FIG. 14 is an explanatory diagram illustrating a positional relationship between the eardrum and a temperature measureable range by a radiation thermometer.
Figure 15:
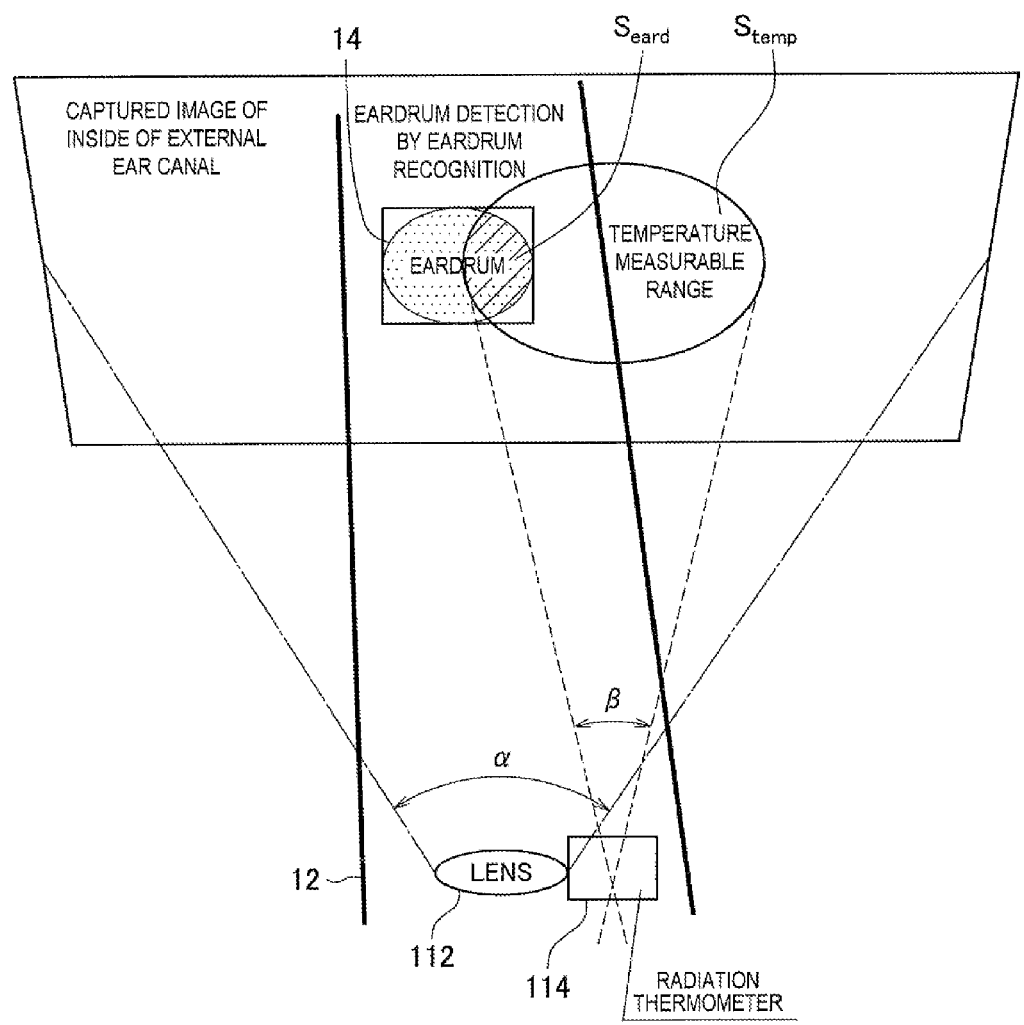
FIG. 15 is an explanatory diagram illustrating a state in which part of the eardrum is included in the temperature measureable range by the radiation thermometer.
Figure 16:
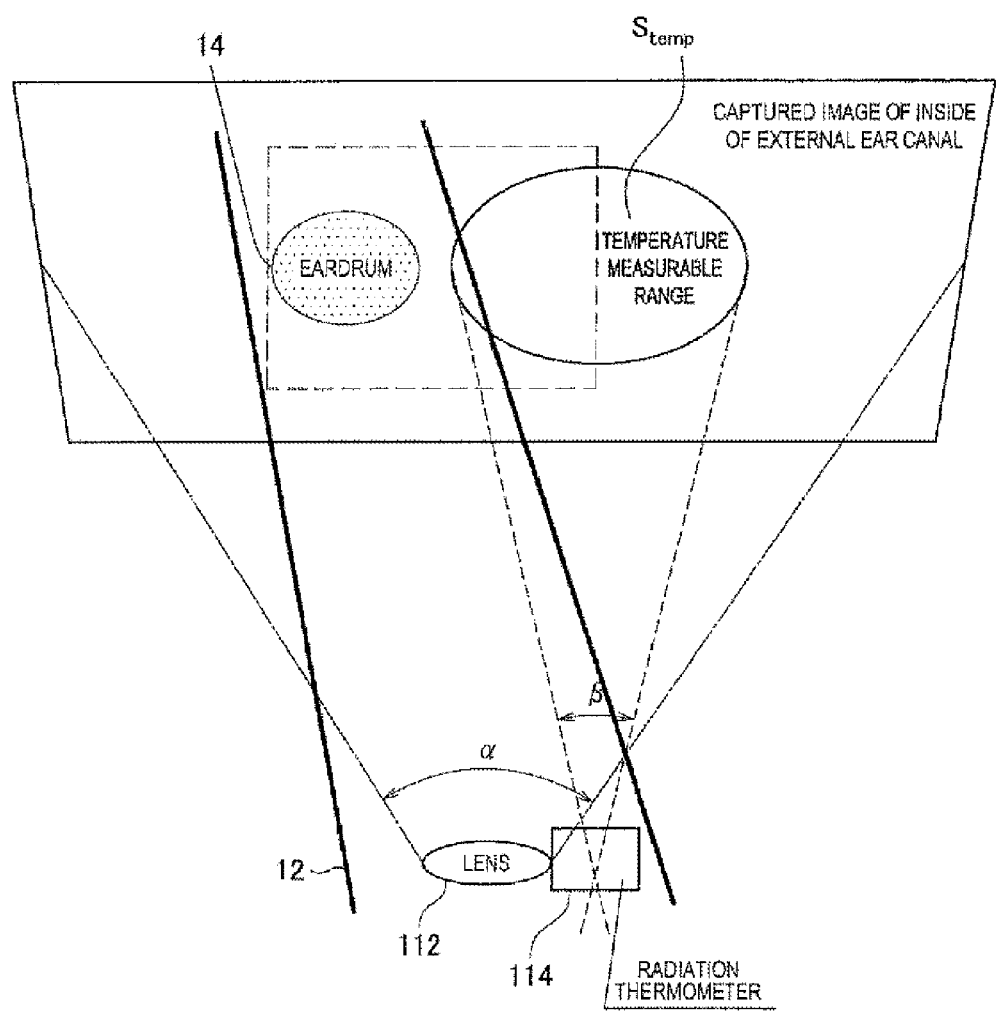
FIG. 16 is an explanatory diagram illustrating a state in which the eardrum is not included in the temperature measureable range by the radiation thermometer.

The tracking of the eardrum 14 will be specifically described based on FIGS. 14 to 16. The tracking is executed when the position of the eardrum 14 is specified in the eardrum recognition process, and continuously performed until sight of the eardrum 14 is lost. FIG. 14 is an explanatory diagram illustrating the eardrum occupancy rate, and illustrates a state in which the temperature sensor unit 110 is inserted into the external ear canal 12 and faces the eardrum 14. At this time, it is assumed that an angle of view of the lens 112 of the temperature sensor unit 110 is a and a temperature measureable angle of the radiation thermometer 114 is β (<α). According to the angle of view of the lens 112, a size of an image captured by the CMOS image sensor 113 (a captured image of the inside of the external ear canal) is determined. On the other hand, a temperature measureable range of the radiation thermometer 114 is determined by the temperature measureable angle β.

An eardrum occupancy rate $O_R$ is represented by an eardrum area $S_{eard}$ within the temperature measurable range compared to a temperature measureable area $S_{temp}$ ($O_R = S_{eard}/S_{temp}$). Accordingly, when the eardrum area $S_{eard}$ included in the temperature measurable range is smaller, the eardrum occupancy rate $O_R$ is lower. For example, as illustrated in FIG. 15, when the temperature sensor unit 110 within the external ear canal 12 does not sufficiently face the eardrum 14, only part of the eardrum 14 is included in the temperature measureable range of the radiation thermometer 114. In addition, as illustrated in FIG. 16, when the direction of the temperature sensor unit 110 inserted into the external ear canal 12 is different from a direction in which the eardrum 14 is directed, the eardrum 14 is also considered not to be included in the temperature measureable range of the radiation thermometer 114. When the eardrum occupancy rate $O_R$ is less than a predetermined value, the measured temperature of the radiation thermometer 114 is far from an actual eardrum temperature and an accurate eardrum temperature is not measurable.

Therefore, because the eardrum 14 is tracked when the position of the eardrum 14 is specified according to the eardrum recognition process, the eardrum recognition unit 221 extracts a detected feature quantity of a luminance gradient or the like of the eardrum 14 based on the eardrum recognition result. Therefore, the eardrum recognition unit 221 tracks the eardrum 14 by searching for the eardrum 14 only in the vicinity thereof based on the extracted feature quantity. When the position of the eardrum 14 for the temperature measurable range is specified according to the tracking, the eardrum recognition unit 221 calculates an accurate direction of the temperature sensor unit 110 so that the eardrum 14 is in the temperature measureable range of the radiation thermometer 114. Therefore, the eardrum recognition unit 221 outputs the calculated accurate direction of the temperature sensor unit 110 to the notification unit 225.

When sight of the eardrum 14 is lost during the tracking, the eardrum recognition unit 221 executes the eardrum recognition process again. Alternatively, the eardrum recognition unit 221 may reset the position of the eardrum 14 by executing the eardrum recognition process after a predetermined time has elapsed from the start of the tracking even when the sight of the eardrum 14 is lost. Because the tracking process is performed using simpler information than in the eardrum recognition process, the eardrum recognition process is superior to the tracking in terms of precision. Thus, because the position of the eardrum 14 is accurately recognized, it is preferable to recognize the position of the eardrum 14 according to the eardrum recognition process periodically even during the tracking.

Returning to the description of FIG. 11, when the eardrum 14 is recognized in step S106, the eardrum recognition unit 221 records the recognition result of the eardrum 14 on the temperature/eardrum state recording unit 224 (S107). The measurement time acquired in step S101 and the eardrum temperature measured in step S102 are also recorded on the temperature/eardrum state recording unit 224. Thereafter, the eardrum recognition unit 221 notifies the user of the eardrum recognition result via the notification unit 225 (S108). Therefore, the eardrum recognition unit 221 checks whether there is an instruction to end the temperature measurement process, the process from step S100 is iteratively executed if there is no end instruction, and the process illustrated in FIG. 11 ends if there is an end instruction (S109).

As described above, in the eardrum temperature processing apparatus in accordance with this embodiment, the eardrum recognition process of recognizing the position of the eardrum 14 is performed and the eardrum temperature of the eardrum 14 is measured. It is possible to reliably measure the eardrum temperature by recognizing an image of the eardrum from image information regarding the eardrum 14 and performing temperature measurement. In addition, the user is notified of a position state of the temperature sensor unit 110 for the eardrum 14, and notified of an adjustment instruction so that the temperature sensor unit 110 is accurately directed to the eardrum 14 when there is a deviation. It is possible to accurately measure a temperature by recognizing a state in which the eardrum temperature is not accurately measureable as described above and allowing the user to adjust an attachment state of a device.

Further, it is possible to perform history management on a time change in the eardrum temperature by outputting the measurement time to the temperature/eardrum state recording unit 224 along with the eardrum temperature and the image information and storing the output measurement time in the storage medium. Accordingly, for example, it is possible to perform analysis of daily fluctuation in a body temperature by attaching the auricle-worn device 100 for a long time and measuring the eardrum temperature at fixed intervals.

(1-C) Correction of Measured Temperature

The eardrum temperature processing apparatus illustrated in FIG. 7 calculates an eardrum temperature based on an occupancy rate (eardrum occupancy rate) in an image of the eardrum 14 recognized in the eardrum recognition process and the measured temperature from the temperature measurement unit 216. Here, the eardrum temperature processing apparatus may further include a correction unit that corrects an eardrum temperature calculated according to a magnitude of an area in which the eardrum 14 is shown. It is possible to calculate the eardrum temperature with a higher precision by including the above-described correction unit. The above-described tracking is also performed to recognize how far the temperature measurable range of the radiation thermometer 114 is from a range of the eardrum 14. The correction unit determines how much the measured temperature should be corrected according to a distance between the temperature measurable range and the range of the eardrum 14.

Figure 17:
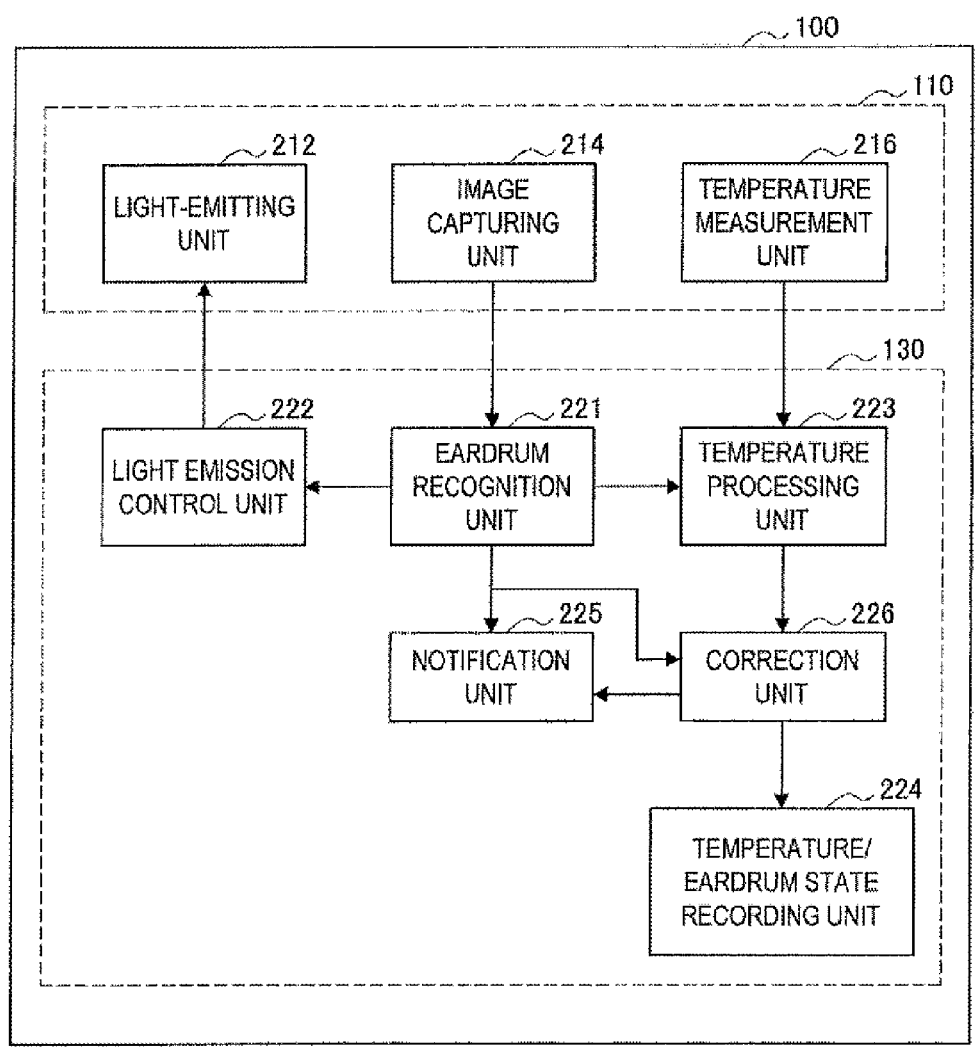
FIG. 17 is a block diagram illustrating a configuration of an eardrum temperature processing apparatus including a correction unit that corrects an eardrum temperature.

A configuration example of the eardrum temperature processing apparatus including the correction unit that corrects the eardrum temperature is illustrated in FIG. 17. The eardrum temperature processing apparatus illustrated in FIG. 17 is different from the eardrum temperature processing apparatus of FIG. 7 in that the correction unit is included. Because configurations and functions of the other functional units are the same, description thereof is omitted here.

Figure 18:
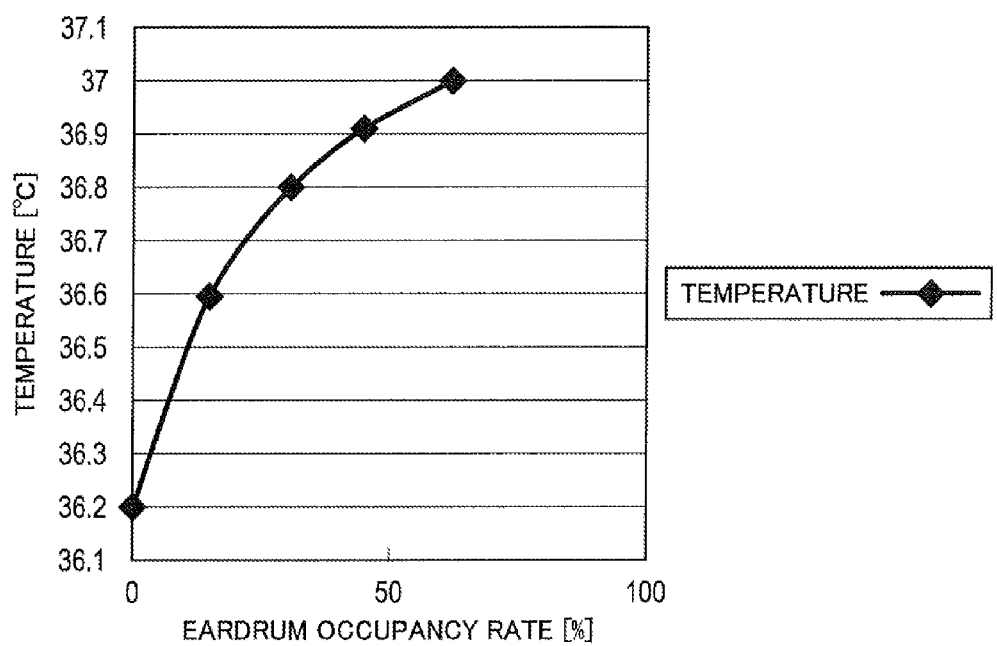
FIG. 18 is a graph illustrating an example of a correlation relationship between an eardrum occupancy rate and an eardrum temperature.

The correction unit 226 corrects the eardrum temperature based on the eardrum occupancy rate, which is a ratio of an area in which the eardrum is shown in a captured image. The correction unit 226 corrects a temperature according to the eardrum occupancy rate in the captured image to determine the eardrum temperature based on the recognition result of the eardrum recognition process of the eardrum recognition unit 221, the eardrum temperature determined by the temperature processing unit 223, and the measured temperature from the temperature measurement unit 216. There is a correlation relationship between the eardrum occupancy rate and the eardrum temperature. The correction unit 226 can correct the measured temperature based on the correlation relationship. An example of the correlation relationship between the eardrum occupancy rate and the eardrum temperature is illustrated in FIG. 18. When the horizontal axis represents an eardrum occupancy rate [%] and the vertical axis represents an eardrum temperature [° C.], the graph of FIG. 18 illustrates a relationship therebetween. It can be seen that the eardrum temperature is also higher when the eardrum occupancy rate is higher.

The correlation relationship between the eardrum occupancy rate and the eardrum temperature may be created while the eardrum temperature is measured for each person whose eardrum temperature is measured. According to the result of the eardrum recognition process and the tracking, the eardrum temperature is also measured along with the position of the eardrum 14 and the eardrum occupancy rate. Therefore, it is possible to precisely perform temperature correction by measuring the correlation relationship between the eardrum occupancy rate and the eardrum temperature as illustrated in FIG. 18 while a position in which the eardrum occupancy rate is high is initially searched for and creating the correlation relationship between the eardrum occupancy rate and the eardrum temperature unique to the person whose eardrum temperature is measured. Because the correlation relationship between the eardrum occupancy rate and the eardrum temperature is likely to change even when measurement is performed on the same person, it is desirable to create the correlation relationship for every measurement time of the eardrum temperature and appropriately update the correlation relationship.

When the correlation relationship between the eardrum occupancy rate and the eardrum temperature as illustrated in FIG. 18 is obtained, the eardrum recognition unit 221, for example, calculates the eardrum occupancy rate according to the eardrum recognition process or the tracking. The correction unit 226 calculates a temperature difference between a measured temperature at the calculated eardrum occupancy and a temperature when the eardrum occupancy rate is highest by referring to the correlation relationship between the eardrum occupancy rate and the eardrum temperature. For example, in FIG. 18, when the temperature at the highest eardrum occupancy rate is 37° C. and the eardrum occupancy rate is 20%, the measured temperature is 0.4° C. lower than 37° C. That is, when the eardrum occupancy rate is lower, the measured temperature is lower than an actual eardrum temperature. Therefore, the correction unit 226 corrects the measured temperature based on the calculated eardrum occupancy rate. For example, when the eardrum occupancy rate is 20% and the measured temperature is 36.4° C., the correction unit 226 adds an amount (in this case, 0.4° C.) by which the measured temperature is lower than the actual eardrum temperature to the measured temperature of 36.4° C., and hence the temperature of 36.8° C. after the addition is given as the eardrum temperature.

After correcting the measured temperature based on the correlation relationship and calculating the eardrum temperature, the correction unit 226 outputs the eardrum temperature and the eardrum recognition result from the eardrum recognition unit 221 to the temperature/eardrum state recording unit 224. In addition, the eardrum temperature after the correction is also output to the notification unit 225 and the user is notified thereof. As described above, it is possible to acquire a more accurate eardrum temperature by providing the correction unit 226 to correct the measured temperature.

The configuration of the eardrum temperature processing apparatus that performs the eardrum recognition process using the captured image and the process of measuring the temperature of the eardrum 14 according to the configuration have been described above.

Figure 19:
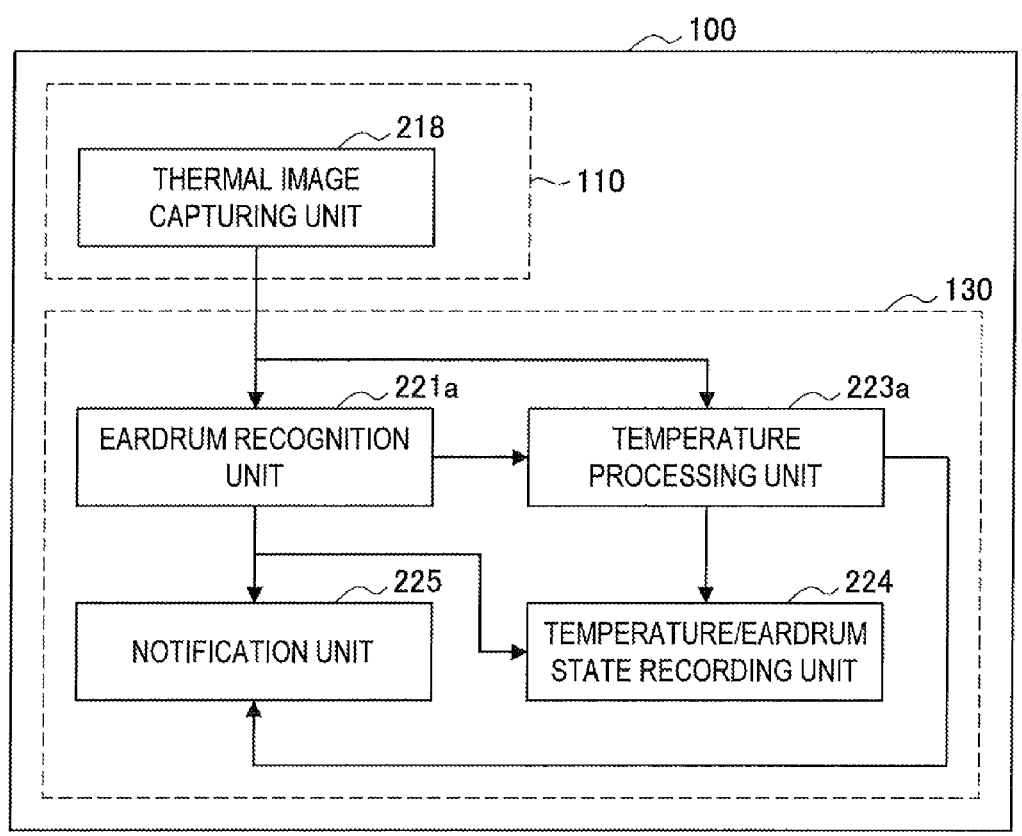
FIG. 19 is a block diagram illustrating a configuration of an eardrum temperature processing apparatus that performs an eardrum recognition process using a thermal image.

(2) Eardrum Temperature Processing Apparatus that Performs Eardrum Recognition Process Using Thermal Image
(2-A) Configuration of Eardrum Temperature Processing Apparatus First, the configuration of the eardrum temperature processing apparatus that performs the eardrum recognition process using the thermal image will be described based on FIG. 19. FIG. 19 is a block diagram illustrating the configuration of the eardrum temperature processing apparatus that performs the eardrum recognition process using the thermal image.

First, the eardrum temperature processing apparatus provided in the auricle-worn device 100 includes a thermal image capturing unit 218 in the temperature sensor unit 110 as illustrated in FIG. 19. The thermal image capturing unit 218 is a detection unit that acquires a thermal image including the eardrum 14 as image information, and, for example, can include a detection element such as a bolometer or a thermopile. Because the thermal image is visually displayed as an image of a temperature distribution of an object, it is possible to simultaneously acquire a position of the eardrum and a measured temperature. The thermal image capturing unit 218 outputs the acquired thermal image to the information processing unit 130.

Figure 20:
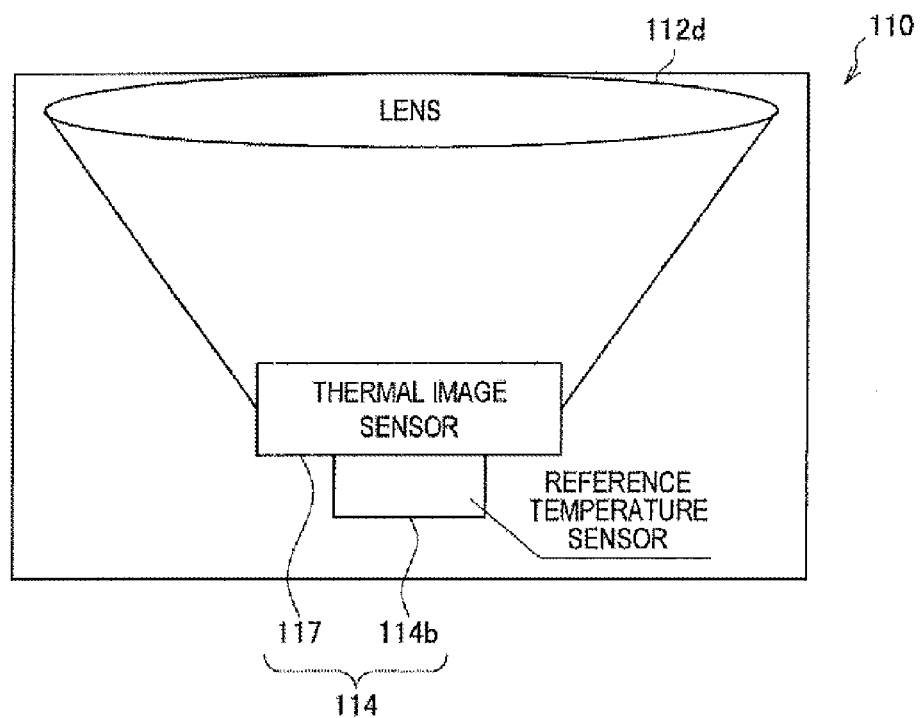
FIG. 20 is an explanatory diagram illustrating a specific configuration example of a temperature sensor unit that acquires a thermal image.

Here, a specific configuration example of the temperature sensor unit 110 is illustrated in FIG. 20. For example, as illustrated in FIG. 20, for the temperature sensor unit 110, a lens 112*d* and a thermal image sensor 117 are provided as the thermal image capturing unit 218. In the thermal image sensor 117, an image acquisition unit having an image acquisition function and a temperature measurement unit having a temperature measurement function are implemented by one device. For infrared-domain light emitted from a human body, an image is formed on the thermal image sensor 117 via the lens 112*d* and converted into an electric signal, and the electric signal is output to the information processing unit 130.

Returning to the description of FIG. 19, the information processing unit 130 includes an eardrum recognition unit 221*a*, a temperature processing unit 223*a*, a temperature/eardrum state recording unit 224, and a notification unit 225. Because the temperature/eardrum state recording unit 224 and the notification unit 225 have the same configurations and functions as those of the eardrum temperature processing apparatus using the captured image illustrated in FIG. 7, description thereof is omitted here.

The eardrum recognition unit 221*a* determines whether a tip end of the temperature sensor unit 110 faces the eardrum 14, and controls the functional units based on the determination result. The eardrum recognition unit 221*a* acquires a thermal image as image information including the eardrum 14 from the thermal image acquisition unit 218 and recognizes the position of the eardrum 14. The eardrum recognition process can be performed as in the eardrum recognition process on the above-described captured image. This process will be described later. The eardrum recognition unit 221*a* performs the image recognition process on the acquired thermal image, and calculates a ratio occupied by the eardrum 14 (an eardrum occupancy rate) in the image. Therefore, the eardrum recognition unit 221*a* outputs the calculated eardrum occupancy rate to at least one of the notification unit 225 and the temperature/eardrum state recording unit 224.

The temperature processing unit 223*a* calculates the eardrum temperature based on the thermal image. As will be described later, in the case of the thermal image, a temperature measurable range corresponds to a captured image. The temperature processing unit 223a calculates a region of the eardrum 14 for the thermal image from the result of the eardrum recognition process, and outputs an average temperature within the eardrum region as the eardrum temperature to the temperature/eardrum state recording unit 224.

Figure 21:
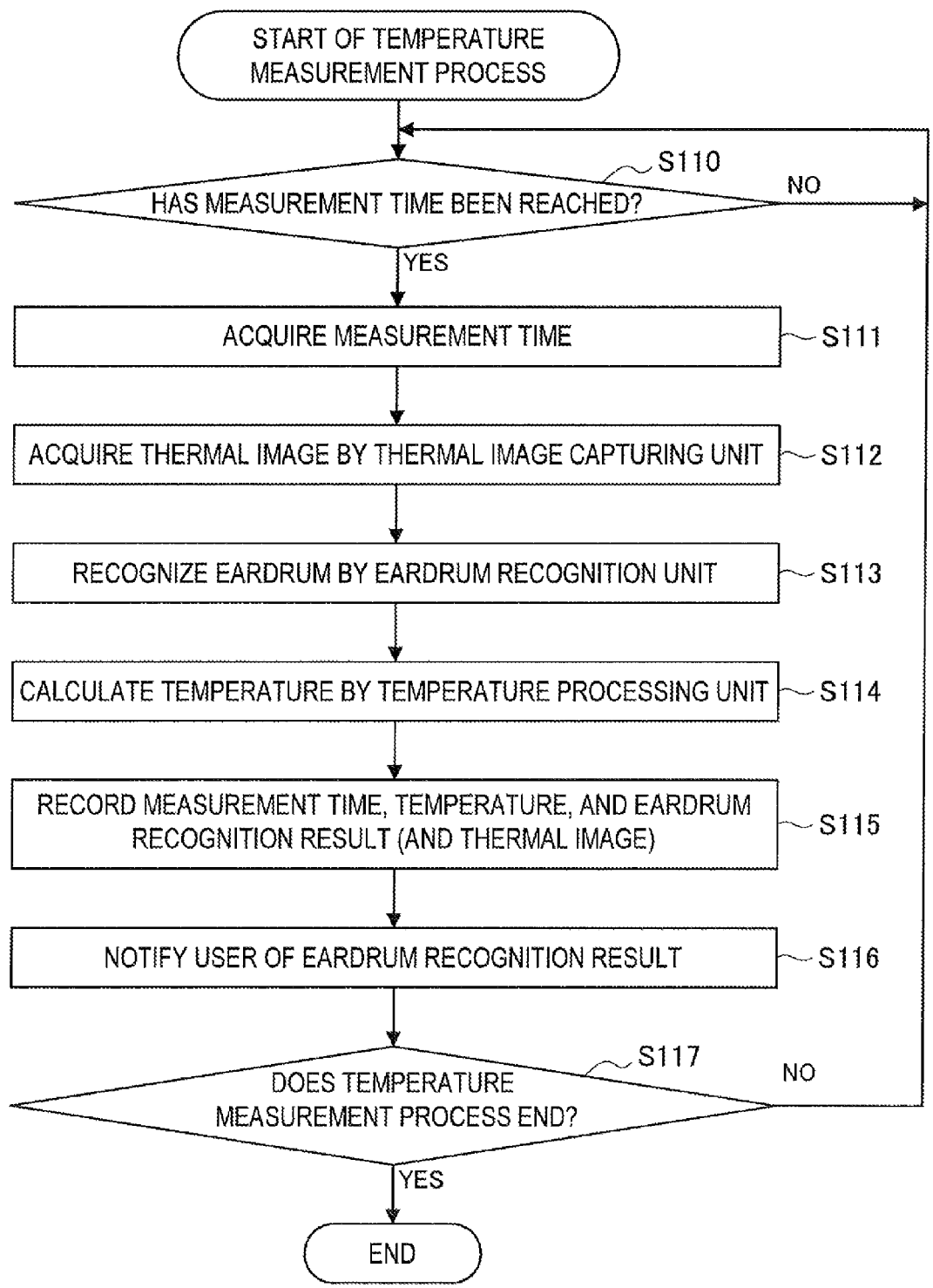
FIG. 21 is a flowchart illustrating a temperature measurement process by the eardrum temperature processing apparatus using a thermal image.

(2-B) Temperature Measurement Process by Eardrum Temperature Processing Apparatus The temperature measurement process by the eardrum temperature processing apparatus illustrated in FIG. 19 will be described based on FIG. 21. FIG. 21 is a flowchart illustrating the temperature measurement process by the eardrum temperature processing apparatus using the thermal image. The detailed description of the same process as the temperature measurement process by the eardrum temperature processing apparatus using the captured image described based on FIG. 11 is omitted.

The temperature measurement process by the eardrum temperature processing apparatus using the thermal image is started when a measurement time has been reached as illustrated in FIG. 21 (S110). The measurement time, for example, such as every second, every minute, or a designated time set by the user, can be arbitrarily set. The eardrum recognition unit 221a iteratively executes the process of step S110 when not reaching the measurement time. When reaching the measurement time, the measurement time is acquired (S111), and thereafter, the thermal image capturing unit 218 acquires the thermal image (S112). When acquiring the thermal image, the thermal image capturing unit 218 outputs the thermal image to the information processing unit 130.

The information processing unit 130 receiving the input of the thermal image from the thermal image capturing unit 218 performs the eardrum recognition process based on the thermal image according to the eardrum recognition unit 221a (S113). The eardrum recognition process can be performed as in the above-described step S106 of FIG. 11. That is, a thermal image, an image in which only a half of the eardrum is shown, an image in which only the external ear canal is shown, and the like are collected in a large volume. The user labels the images one by one in advance by cutting the image into a part which is the eardrum 14 and a part which is not the eardrum 14. By creating a classifier created by statistically learning the above, the eardrum recognition unit 221a can recognize the position of the eardrum 14 from the thermal image.

Figure 22:
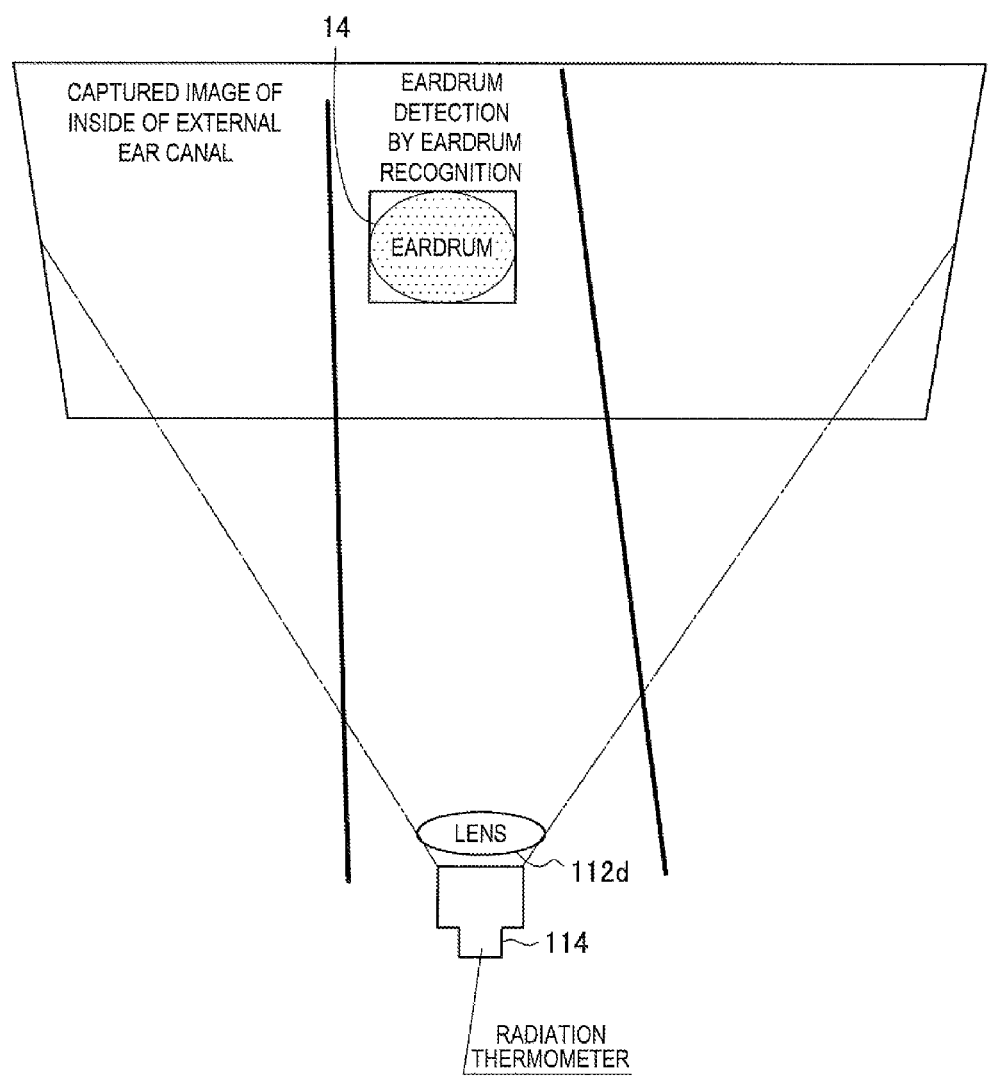
FIG. 22 is an explanatory diagram illustrating a relationship between a thermal image and an eardrum region within the thermal image.

Then, when the eardrum 14 is recognized in step S114, the temperature processing unit 223a calculates an eardrum temperature (S114). FIG. 22 illustrates a relationship between a thermal image and a region of the eardrum 14 (an eardrum region) within the thermal image. As illustrated in FIG. 22, in the thermal image, a range of the thermal image becomes a temperature measureable range. While only one measured value can be acquired in the case of the temperature sensor, temperature information can be acquired at an image resolution in the thermal image. The temperature processing unit 223a obtains the eardrum region for the thermal image from the eardrum recognition processing result, and sets an average value of temperatures within the eardrum region to the eardrum temperature.

The eardrum recognition unit 221a records the recognition result of the eardrum 14 on the temperature/eardrum state recording unit 224 (S115). On the temperature/eardrum state recording unit 224, the measurement time acquired in step S111 and the eardrum temperature measured in step S113 are also recorded. Thereafter, the eardrum recognition unit 221a notifies the user of the eardrum recognition result via the notification unit 225 (S116). Therefore, the eardrum recognition unit 221a checks whether there is an instruction to end the temperature measurement process, the process from step S110 is iteratively executed if there is no end instruction, and the process illustrated in FIG. 21 ends if there is an end instruction (S117).

As described above, in the eardrum temperature processing apparatus using the thermal image, the eardrum recognition process of recognizing the position of the eardrum from the thermal image is performed and the eardrum temperature of the eardrum 14 is measured. As described above, it is possible to more accurately measure the eardrum temperature by checking whether the temperature sensor unit 110 is directed to the eardrum 14 and determining the eardrum temperature. In addition, the user is notified of a position state of the temperature sensor unit 110 for the eardrum 14, and notified of an adjustment instruction so that the temperature sensor unit 110 is accurately directed to the eardrum 14 when there is a deviation. As described above, it is possible to accurately measure a temperature by recognizing a state in which the eardrum temperature is not accurately measureable and allowing the user to adjust an attachment state of a device. Further, it is possible to perform history management on a time change in the eardrum temperature by outputting the measurement time to the temperature/eardrum state recording unit 224 along with the eardrum temperature and the image information and storing the output measurement time in the storage medium. Accordingly, for example, it is possible to perform analysis of daily fluctuation in the body temperature by attaching the auricle-worn device 100 for a long time and measuring the eardrum temperature at fixed intervals.

<3. Hardware Configuration Example>

Figure 23:
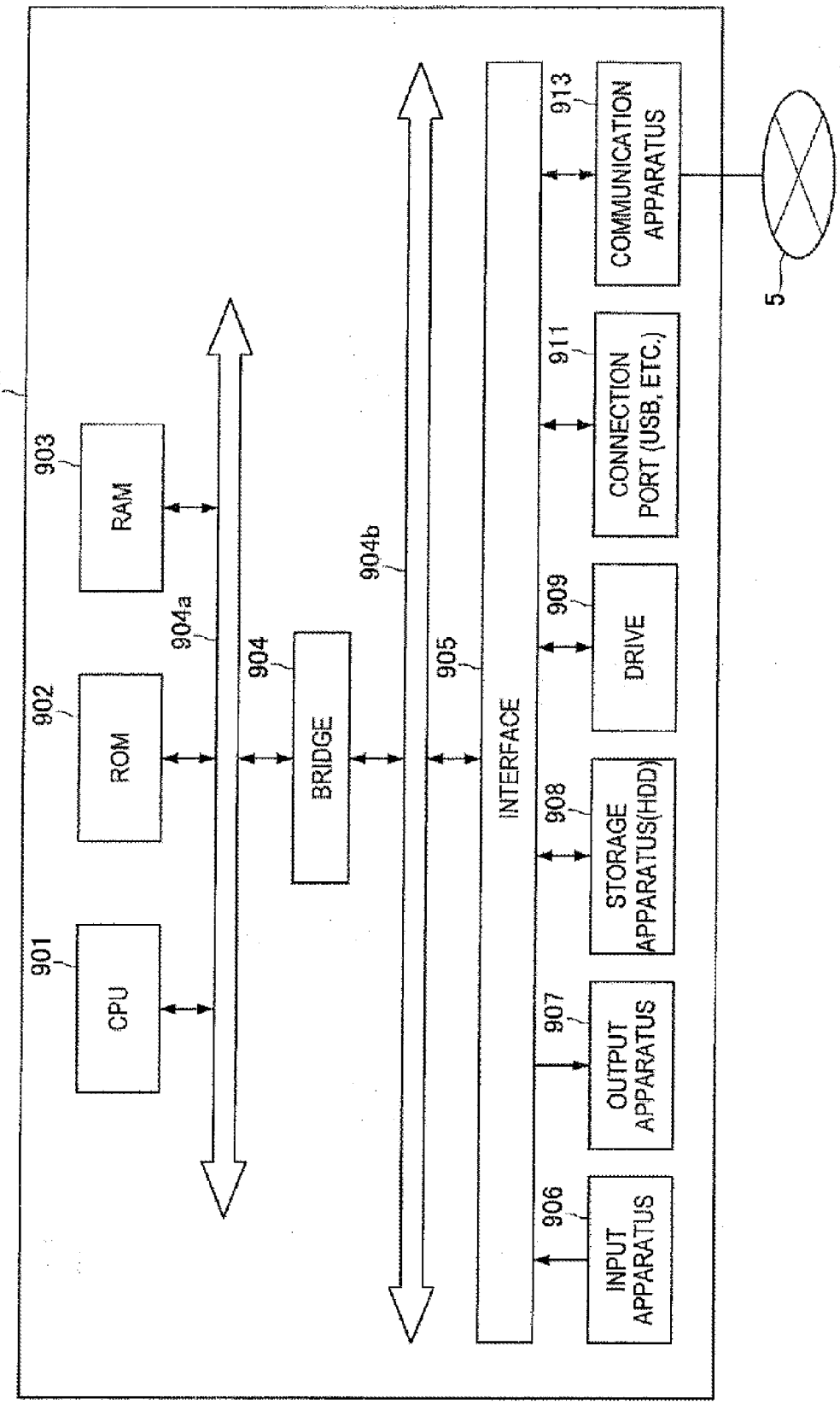
FIG. 23 is a hardware configuration diagram illustrating a hardware configuration example of the eardrum temperature processing apparatus in accordance with the same embodiment.

A process by the eardrum temperature processing apparatus in accordance with this embodiment can also be executed by hardware or software. In this case, the eardrum temperature processing apparatus can also be configured as illustrated in FIG. 23. Hereinafter, the hardware configuration example of the eardrum temperature processing apparatus in accordance with this embodiment will be described based on FIG. 23.

The eardrum temperature processing apparatus in accordance with this embodiment can be implemented by a processing apparatus such as a computer as described above. As illustrated in FIG. 23, the eardrum temperature processing apparatus includes a central processing unit (CPU) 901, a read only memory (ROM) 902, a random access memory (RAM) 903, and a host bus 904a. In addition, the eardrum temperature processing apparatus includes a bridge 904, an external bus 904b, an interface 905, an input apparatus 906, an output apparatus 907, a storage apparatus (hard disk drive (HDD)) 908, a drive 909, a connection port 911, and a communication apparatus 913.

The CPU 901 functions as an arithmetic processing apparatus and a control apparatus, and controls the overall operation of the eardrum temperature processing apparatus according to various programs. In addition, the CPU 901 may be a microprocessor. The ROM 902 stores programs, arithmetic parameters, and the like for use by the CPU 901. The RAM 903 temporarily stores a program for use in execution of the CPU 901 and parameters that change appropriately during the execution. These components are mutually connected through the host bus 904a including a CPU bus or the like.

The host bus 904a is connected to the external bus 904b such as a peripheral component interconnect/interface (PCI) via the bridge 904. The host bus 904a, the bridge 904, and the external bus 904b are not necessarily configured separately, and these functions may be implemented by one bus.

The input apparatus 906 includes an input mechanism for allowing the user to input information such as a mouse, a keyboard, a touch panel, a button, a microphone, a switch, and a lever, an input control circuit for generating an input signal based on the user's input and outputting the generated input signal to the CPU 901, and the like. The output apparatus 907, for example, includes a liquid crystal display (LCD) apparatus, an organic light emitting diode (OLED) apparatus, a display apparatus such as a lamp, and a sound output apparatus such as a speaker.

The storage apparatus 908 is an example of the storage unit of the eardrum temperature processing apparatus, and is a data storage apparatus. The storage apparatus 908 can include a storage medium, a recording apparatus for recording data on the storage medium, a read apparatus for reading data from the storage medium, and an erasing apparatus for erasing data recorded on the storage medium. The storage apparatus 908, for example, includes an HDD. This storage apparatus 908 drives a hard disk, and stores a program to be executed by the CPU 901 and various data.

The drive 909 is a reader/writer for the storage medium and embedded in the eardrum temperature processing apparatus or attached externally thereto. The drive 909 reads information recorded on a removable recording medium such as a magnetic disk, an optical disc, a magneto-optical disc or a semiconductor memory, and outputs the read information to the RAM 903.

The connection port 911 is an interface connected to an external device, and, for example, is a connection port to an external device to which data can be transmitted using a USB or the like. In addition, the communication apparatus 913, for example, is a communication interface including a communication device for connecting to a communication network 5 and the like. In addition, the communication apparatus 913 may be a communication apparatus corresponding to wireless LAN, a communication apparatus corresponding to wireless USB, or a wired communication apparatus that executes wired communication.

The preferred embodiments of the present disclosure have been described above with reference to the accompanying drawings, whilst the present disclosure is not limited to the above examples, of course. It should be understood by those skilled in the art that various modifications, combinations, sub-combinations and alterations may occur depending on design requirements and other factors insofar as they are within the scope of the appended claims or the equivalents thereof.

Additionally, the present technology may also be configured as below.

(1) An information processing apparatus including:
an eardrum recognition unit configured to recognize a position of an eardrum based on image information regarding the eardrum;
a temperature measurement unit configured to acquire a temperature within an external ear canal including the eardrum; and
a temperature processing unit configured to determine a temperature of the eardrum based on a recognition result of the eardrum recognition unit and a measured temperature of the temperature measurement unit.

(2) The information processing apparatus according to (1), wherein the image information regarding the eardrum is a captured image including the eardrum, and
wherein the eardrum recognition unit recognizes the position of the eardrum based on the captured image.

(3) The information processing apparatus according to (2), including:
an imaging unit configured to acquire the image information regarding the eardrum.

(4) The information processing apparatus according to (1), wherein the image information regarding the eardrum is a thermal image including the eardrum,
wherein the eardrum recognition unit recognizes the position of the eardrum based on the thermal image, and
wherein the temperature measurement unit acquires a temperature within an ear canal including the eardrum based on the thermal image.

(5) The information processing apparatus according to (4), wherein acquisition of the image information regarding the eardrum and temperature measurement by the temperature measurement unit are performed by an identical device.

(6) The information processing apparatus according to any one of (1) to (5), including:
a notification unit configured to notify a user of eardrum information regarding the eardrum,
wherein the notification unit provides at least notification of a calculated temperature of the eardrum.

(7) The information processing apparatus according to (6), wherein the eardrum recognition unit calculates an eardrum occupancy rate representing a ratio occupied by the eardrum in a predetermined range in an image of the eardrum based on a recognition result of the image information regarding the eardrum, and
wherein the notification unit notifies the user of a position state of the temperature measurement unit with respect to the eardrum based on the eardrum occupancy rate.

(8) The information processing apparatus according to (7), wherein the notification unit notifies the user of a direction for adjusting the direction of the temperature measurement unit in a manner that the eardrum occupancy rate increases.

(9) The information processing apparatus according to any one of (1) to (8), further including:
a correction unit configured to correct the temperature of the eardrum calculated by the temperature processing unit,
wherein the eardrum recognition unit calculates an eardrum occupancy rate representing a ratio occupied by the eardrum in a predetermined range in an image of the eardrum based on a recognition result of the image information regarding the eardrum, and
wherein the correction unit corrects the temperature of the eardrum calculated by the temperature processing unit based on the eardrum occupancy rate.

(10) The information processing apparatus according to (9), wherein the correction unit corrects the temperature of the eardrum based on a correlation relationship between the eardrum occupancy rate and the temperature of the eardrum.

What is claimed is:
1. An information processing apparatus comprising:
an image sensor operable to capture an image of an eardrum;
a temperature sensor; and
a central processing unit (CPU) operable to:
acquire image information regarding the eardrum from the captured image of the eardrum;
determine a first area corresponding to a temperature measurable area of the temperature sensor in the captured image;
determine a second area occupied by the eardrum within the first area corresponding to the temperature measurable area of the temperature sensor based on the acquired image information;
calculate an eardrum occupancy rate, wherein the eardrum occupancy rate represents a ratio of the second area to the first area;

acquire a temperature, within an external ear canal including the eardrum, measured by the temperature sensor; and determine a temperature of the eardrum based on, the calculated eardrum occupancy rate, and the acquired temperature.

2. The information processing apparatus according to claim 1,
wherein the CPU recognizes a position of the eardrum based on the captured image.

3. The information processing apparatus according to claim 1,
wherein the acquired image information regarding the eardrum is a thermal image including the eardrum,
wherein the CPU recognizes a position of the eardrum based on the thermal image, and
wherein the CPU acquires a temperature within the external ear canal including the eardrum based on the thermal image.

4. The information processing apparatus according to claim 3, wherein the CPU is operable to:
acquire the image information regarding the eardrum and determine the temperature from the captured image of the eardrum, simultaneously.

5. The information processing apparatus according to claim 1, wherein the CPU is further operable to:
notify a user of the acquired image information regarding the eardrum, wherein the CPU provides at least notification of the determined temperature of the eardrum.

6. The information processing apparatus according to claim 1,
wherein the CPU notifies a user of a position state of the temperature sensor with respect to the eardrum based on the calculated eardrum occupancy rate.

7. The information processing apparatus according to claim 6,
wherein the CPU notifies the user of a direction for adjusting the direction of the temperature sensor in a manner that the eardrum occupancy rate increases.

8. The information processing apparatus according to claim 1, wherein the CPU is operable to:
correct the determined temperature of the eardrum,
wherein the CPU corrects the determined temperature of the eardrum based on the calculated eardrum occupancy rate.

9. The information processing apparatus according to claim 8,
wherein the CPU corrects the determined temperature of the eardrum based on a correlation relationship between the calculated eardrum occupancy rate and the acquired temperature of the eardrum.

10. An information processing method comprising:
capturing an image of an eardrum;
acquiring image information regarding the eardrum from the captured image of the eardrum;
determining a first area corresponding to a temperature measurable area of a temperature sensor in the captured image;
determining a second area occupied by the eardrum within the first area corresponding to the temperature measurable area of the temperature sensor based on the acquired image information;
calculating an eardrum occupancy rate, wherein the eardrum occupancy rate represents a ratio of the second area to the first area;
acquiring a temperature, within an external ear canal including the eardrum, measured by the temperature sensor; and
determining a temperature of the eardrum based on, the calculated eardrum occupancy rate, and the acquired temperature.

11. A non-transitory computer readable medium having stored thereon, a set of computer-executable instructions for causing the computer to perform steps comprising:
capturing an image of an eardrum;
acquiring image information regarding the eardrum from the captured image of the eardrum;
determining a first area corresponding to a temperature measurable area of a temperature sensor in the captured image;
determining a second area occupied by the eardrum within the first area corresponding to the temperature measurable area of the temperature sensor based on the acquired image information;
calculating an eardrum occupancy rate, wherein the eardrum occupancy rate represents a ratio of the second area to the first area;
acquiring a temperature, within an external ear canal including the eardrum, measured by the temperature sensor; and
determining a temperature of the eardrum based on, the calculated eardrum occupancy rate, and the acquired temperature.

* * * * *